United States Patent
Ori et al.

(10) Patent No.: US 11,597,122 B2
(45) Date of Patent: Mar. 7, 2023

(54) MANUFACTURING METHOD OF PLATE PRECURSOR HAVING NEEDLE-LIKE PROTRUSION, AND MANUFACTURING METHOD OF MICRONEEDLE ARRAY

(71) Applicant: FUJIFILM Corporation, Tokyo (JP)

(72) Inventors: Ricardo Itiro Ori, Kanagawa (JP);
Hiroki Yanagawa, Kanagawa (JP);
Kozue Ikeda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 544 days.

(21) Appl. No.: 16/591,634

(22) Filed: Oct. 3, 2019

(65) Prior Publication Data
US 2020/0114547 A1   Apr. 16, 2020

(30) Foreign Application Priority Data
Oct. 15, 2018   (JP) .............................. JP2018-194095

(51) Int. Cl.
*B29C 33/38* (2006.01)
*A61M 37/00* (2006.01)
(Continued)

(52) U.S. Cl.
CPC ..... *B29C 33/3892* (2013.01); *A61M 37/0015* (2013.01); *B24B 19/16* (2013.01);
(Continued)

(58) Field of Classification Search
CPC ............................................ A61M 2037/0053
See application file for complete search history.

(56) References Cited

U.S. PATENT DOCUMENTS

| 7,497,980 B2 | 3/2009 | Xu et al. |
| 7,789,733 B2 | 9/2010 | Sugimura et al. |
| (Continued) | | |

FOREIGN PATENT DOCUMENTS

| CN | 1691970 | 11/2005 |
| JP | 2008114345 | 5/2008 |
| (Continued) | | |

OTHER PUBLICATIONS

Thepsonthi, T., N. Milesi, and T. Özel. "Design and prototyping of micro-needle arrays for drug delivery using customized tool-based micro-milling process." Proceedings of the 1st International Conference on Design and Processes for Medical Devices, at Brescia, Italy. 2012. (Year: 2012).*

(Continued)

*Primary Examiner* — Benjamin A Schiffman
(74) *Attorney, Agent, or Firm* — JCIPRNET

(57) ABSTRACT

Provided are a manufacturing method of a plate precursor having a plurality of needle-like protrusions and a manufacturing method of a microneedle array, which make it possible to manufacture a plate precursor within a short period of time.
A manufacturing method of a plate precursor having a needle-like protrusion includes: a preparation step of preparing a cutting tool including at least one blade conforming to an external shape of the needle-like protrusion, and a base material; and a cutting step of cutting the base material by rotating the cutting tool about a tool axis of the cutting tool and revolving the cutting tool around an axis of the needle-like protrusion to be formed on the base material to form the needle-like protrusion having a shape conforming to a shape of the cutting tool.

10 Claims, 26 Drawing Sheets

(51) Int. Cl.
*B24B 19/16* (2006.01)
*B29C 33/42* (2006.01)
*A61K 9/00* (2006.01)
*B29L 31/00* (2006.01)

(52) U.S. Cl.
CPC ........ *B29C 33/3842* (2013.01); *B29C 33/424* (2013.01); *A61K 9/0021* (2013.01); *A61M 2037/0046* (2013.01); *A61M 2037/0053* (2013.01); *B29L 2031/756* (2013.01); *B29L 2031/7544* (2013.01)

(56) References Cited

U.S. PATENT DOCUMENTS

| | | | |
|---|---|---|---|
| 8,292,696 B2 | 10/2012 | Sugimura et al. | |
| 8,876,575 B2 | 11/2014 | Sugimura et al. | |
| 10,799,691 B2 | 10/2020 | Uemura et al. | |
| 2007/0147965 A1 | 6/2007 | Yamada | |
| 2013/0096532 A1* | 4/2013 | Ozel | A61M 37/0015 604/173 |
| 2018/0215078 A1* | 8/2018 | Ogawa | B29C 41/20 |

FOREIGN PATENT DOCUMENTS

| | | | | |
|---|---|---|---|---|
| JP | 2008237673 | | 10/2008 | |
| JP | 2010057704 | | 3/2010 | |
| JP | 2011143098 | | 7/2011 | |
| JP | 4987916 | | 8/2012 | |
| JP | 5401061 | | 1/2014 | |
| JP | 2014188329 | | 10/2014 | |
| JP | 2017071109 A | * | 4/2017 | |
| JP | 2017209240 | | 11/2017 | |
| JP | 2018042677 | | 3/2018 | |
| WO | 2016072350 | | 5/2016 | |
| WO | WO-2017056894 A1 | * | 4/2017 | ............ A61M 37/00 |

OTHER PUBLICATIONS

"Office Action of Japan Counterpart Application" with English translation thereof, dated Sep. 17, 2021, p. 1-p. 8.
"Search Report of Europe Counterpart Application", dated Apr. 2, 2020, p. 1-p. 7.
Office Action of China Counterpart Application, with English translation thereof, dated Sep. 19, 2022, pp. 1-17.
Office Action of China Counterpart Application, with English translation thereof, dated Nov. 9, 2022, pp. 1-19.

* cited by examiner

FIG. 24
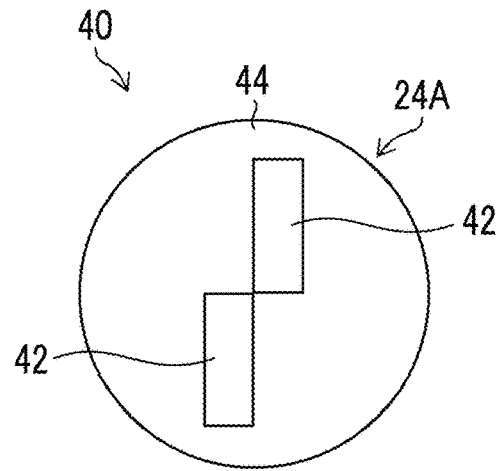
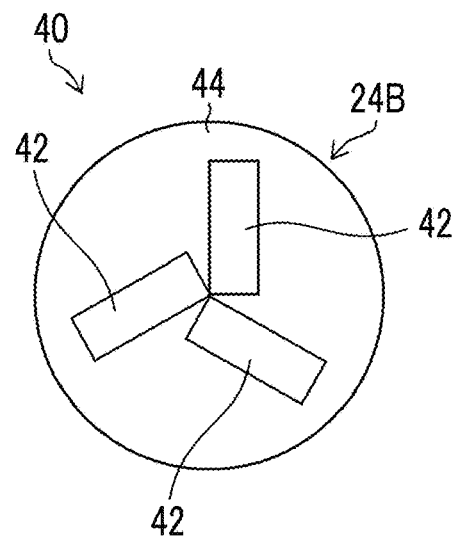
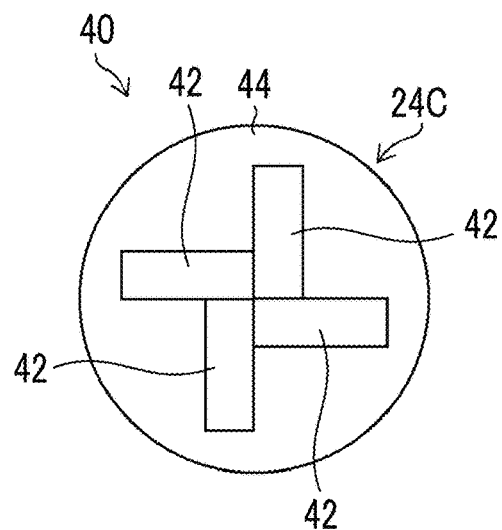

FIG. 31
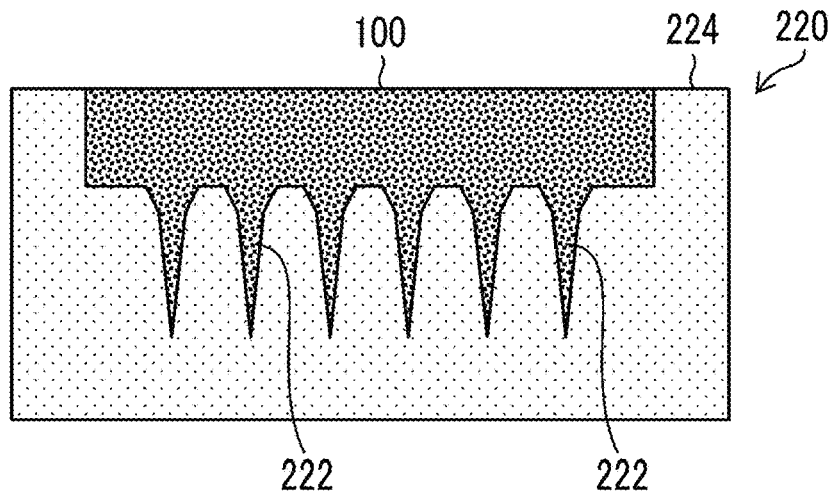
FIG. 32
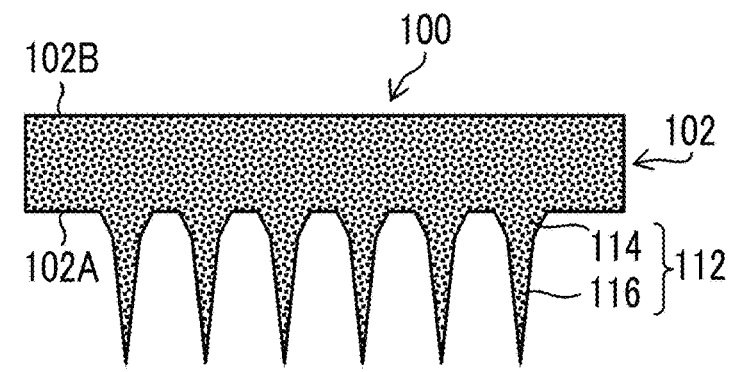
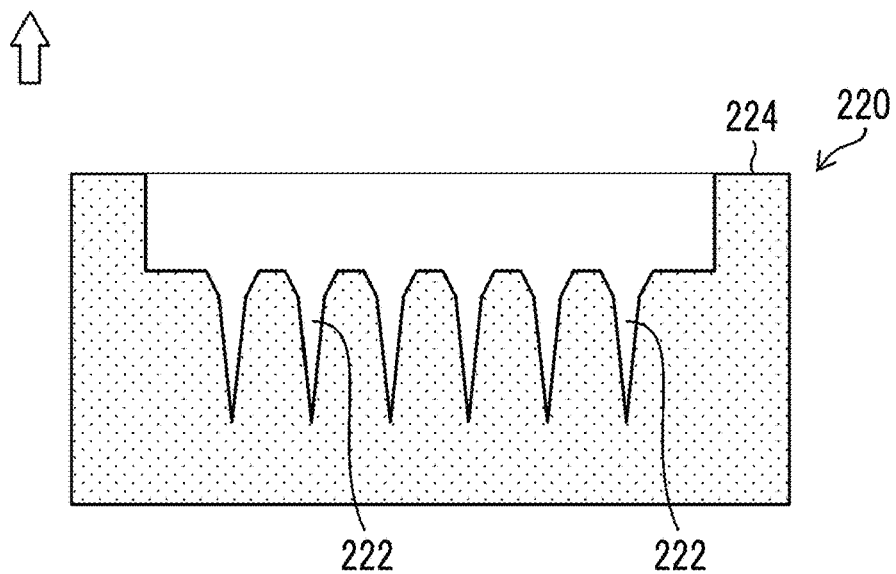

MANUFACTURING METHOD OF PLATE PRECURSOR HAVING NEEDLE-LIKE PROTRUSION, AND MANUFACTURING METHOD OF MICRONEEDLE ARRAY

CROSS-REFERENCE TO RELATED APPLICATIONS

The present application claims priority under 35 U.S.C. § 119 to Japanese Patent Application No. 2018-194095, filed on Oct. 15, 2018. The above application is hereby expressly incorporated by reference, in its entirety, into the present application.

BACKGROUND OF THE INVENTION

1. Field of the Invention

The present invention relates to a manufacturing method of a plate precursor having a needle-like protrusion, and a manufacturing method of a microneedle array.

2. Description of the Related Art

In recent years, as a novel dosage form capable of injecting drugs such as insulin, vaccines, and human growth hormone (hGH) into the skin without pain, a microneedle array has been known. A self-dissolving microneedle array is an array of microneedles (also referred to as fine needles or small needles) which contain drugs and are biodegradable. By attaching this microneedle array to the skin, each microneedle pierces the skin, and these microneedles are absorbed in the skin such that the drugs contained in each microneedle can be administered into the skin. Microneedle arrays are also called percutaneous absorption sheets.

In a case where the above-mentioned microneedle array is manufactured, a plate precursor having a plurality of needle-like protrusions of the same shape as the microneedle array to be manufactured is produced. A resin mold having a plurality of recessed portions is produced from the produced plate precursor. A polymer solution, which is a raw material of the microneedle array, is supplied to the recessed portions of the resin mold. The polymer solution is dried and cured to form the microneedle array on the resin mold. The microneedle array is separated from the resin mold, thereby manufacturing the microneedle array.

Various manufacturing methods for a plate precursor for manufacturing a microneedle array have been proposed. For example, in JP4987916B and JP5401061B, a plate precursor is manufactured by forming linear grooves in a substrate by grinding.

SUMMARY OF THE INVENTION

However, the method using grinding requires moving a grinding wheel in a first direction a plurality of times and further moving the grinding wheel in a second direction intersecting the first direction a plurality of times. Therefore, in the grinding, it takes much time to manufacture the plate precursor.

The present invention has been made taking the above circumstances into consideration, and an object thereof is to provide a manufacturing method of a plate precursor having a needle-like protrusion and a manufacturing method of a microneedle array, which make it possible to manufacture a plate precursor within a short period of time.

A manufacturing method of a plate precursor having a needle-like protrusion according to a first aspect, comprises: a preparation step of preparing a cutting tool comprising at least one blade conforming to an external shape of the needle-like protrusion, and a base material; and a cutting step of cutting the base material by rotating the cutting tool about a tool axis of the cutting tool and revolving the cutting tool around an axis of the needle-like protrusion to be formed on the base material to form the needle-like protrusion having a shape conforming to a shape of the cutting tool. According to the first aspect, the plate precursor having the needle-like protrusion can be manufactured within a short period of time.

In the manufacturing method of a plate precursor having a needle-like protrusion according to a second aspect, a plurality of the needle-like protrusions are formed by repeating the cutting step a plurality of times. According to the second aspect, the plate precursor having the plurality of needle-like protrusions can be manufactured within a short period of time.

In the manufacturing method of a plate precursor having a needle-like protrusion according to a third aspect, a distance between the tool axis and the axis is adjusted in the cutting step. According to the third aspect, the shape of the needle-like protrusion can be controlled.

In the manufacturing method of a plate precursor having a needle-like protrusion according to a fourth aspect, the cutting tool comprising at least one blade comprises a plurality of blades. According to the fourth aspect, the number of blades of the cutting tool can be selected according to the shape of the needle-like protrusion to be manufactured.

In the manufacturing method of a plate precursor having a needle-like protrusion according to a fifth aspect, the cutting tool is moved to an inside of the base material stepwise in parallel to the tool axis, in the cutting step. According to the fifth aspect, the needle-like protrusion can be easily formed on the base material.

In the manufacturing method of a plate precursor having a needle-like protrusion according to a sixth aspect, the stepwise movement of the cutting tool is a continuous movement. According to the sixth aspect, the needle-like protrusion can be formed within a shorter period of time.

In the manufacturing method of a plate precursor having a needle-like protrusion according to a seventh aspect, the stepwise movement of the cutting tool is an intermittent movement. According to the seventh aspect, deformation of the needle-like protrusion during cutting can be suppressed.

In the manufacturing method of a plate precursor having a needle-like protrusion according to an eighth aspect, the cutting tool is changed from a first posture to a second posture by inclining the tool axis to cut the base material by the cutting tool. According to the eighth aspect, the needle-like protrusion having a more preferable shape can be manufactured by improving the degree of freedom of cutting.

A manufacturing method of a microneedle array according to a ninth aspect comprises: a step of preparing a plate precursor manufactured by the manufacturing method of a plate precursor having a needle-like protrusion described above; a step of producing a resin precursor having a needle-like recessed portion from the plate precursor; a step of producing a duplicate mold having a needle-like protrusion from the resin precursor by electroforming; a step of producing a resin mold having a needle-like recessed portion from the duplicate mold; a step of supplying a liquid material to the resin mold; a step of solidifying the liquid material of the resin mold by drying to form a microneedle array; and a step of separating the microneedle array from the resin mold. According to the ninth aspect, the microneedle array can be manufactured within a short period of time.

A manufacturing method of a microneedle array according to a tenth aspect comprises: a step of preparing a plate precursor manufactured by the manufacturing method of a plate precursor having a needle-like protrusion described above; a step of producing a resin mold having a needle-like recessed portion from the plate precursor; a step of supplying a liquid material to the resin mold; a step of solidifying the liquid material of the resin mold by drying to form a microneedle array; and a step of separating the microneedle array from the resin mold. According to the tenth aspect, a step of producing a resin precursor and a duplicate mold is not required.

According to the manufacturing method of a plate precursor according to the aspects of the present invention, it is possible to manufacture a plate precursor having needle-like protrusions within a short period of time.

BRIEF DESCRIPTION OF THE DRAWINGS

FIG. 24 is a view illustrating a shape of a distal end of a blade of a cutting tool.

FIG. 31 is a view for describing a step of the manufacturing method of a first microneedle array.

FIG. 32 is a view for describing a step of the manufacturing method of a first microneedle array.

DESCRIPTION OF THE PREFERRED EMBODIMENTS

Figure 1:
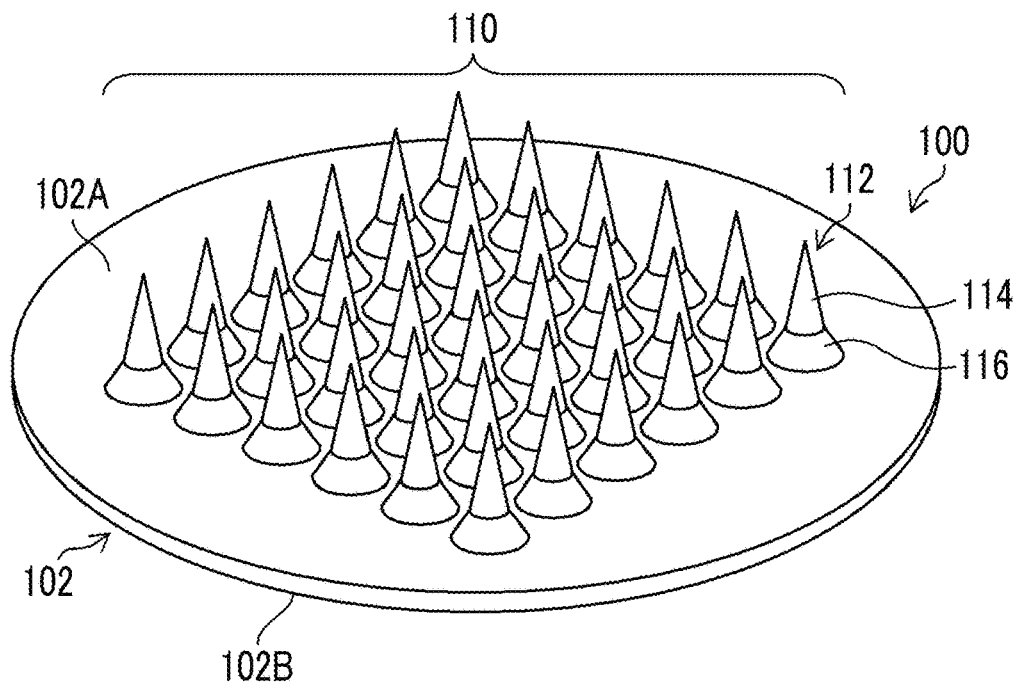
FIG. 1 is a perspective view illustrating an example of a microneedle array.

Hereinafter, preferred embodiments of the present invention will be described with reference to the accompanying drawings. The present invention is described by the following preferred embodiments. Modifications can be made by various methods without departing from the scope of the present invention, and other embodiments than this embodiment can also be used. Therefore, all modifications within the scope of the present invention are included in the appended claims.

Here, in the figures, like elements having similar functions are denoted by like reference numerals. In addition, in this specification, in a case where a numerical value range is expressed using "to", the numerical value range includes the numerical values of the upper limit and the lower limit indicated by "to".

Microneedle Array

An example of a microneedle array (percutaneous absorption sheet) will be described.

FIG. 1 is a perspective view illustrating an example of a microneedle array 100 manufactured using a plate precursor described later. The microneedle array 100 of the embodiment corresponds to a patch for one administration (one patch). The microneedle array 100 includes a sheet-like base portion 102 having a first surface 102A and a second surface 102B, which oppose each other, and a protruding pattern 110.

The term "sheet-like" means a thin flat shape as a whole with respect to the two opposed first and second surfaces 102A and 102B having a large area, and it is not necessary that the first surface 102A and the second surface 102B are perfectly flat. In addition, although the base portion 102 illustrated in FIG. 1 is circular in a plan view, the base portion 102 may be rectangular, polygonal, elliptical, or the like.

The protruding pattern 110 is constituted by a plurality of needle-like protrusions 112 (microneedles) configured to contain a drug. The needle-like protrusions 112 are provided on the first surface 102A. The needle-like protrusion 112 includes a needle portion 114 and a frustum portion 116. The needle portion 114 and the frustum portion 116 constituting the needle-like protrusion 112 are arranged in the order of the frustum portion 116 and the needle portion 114 from the base portion 102.

A plurality of the frustum portions 116 are disposed on the first surface 102A of the microneedle array 100. The frustum portion 116 has two bottom surfaces and has a three-dimensional structure surrounded by a conical surface. The bottom surface (lower bottom surface) of the two bottom surfaces of the frustum portion 116 having a large area is connected to the base portion 102. The bottom surface (upper bottom surface) of the two bottom surfaces of the frustum portion 116 having a small area is connected to the needle portion 114. Of the two bottom surfaces of the frustum portion 116, the area of the bottom surface in a direction away from the base portion 102 is small. The inclination angle (frustum portion angle) of the surface of the frustum portion 116 with respect to the first surface 102A is different from the inclination angle (needle portion angle) of the surface of the needle portion 114 with respect to the first surface 102A. In FIG. 1, the needle portion angle is greater than the frustum portion angle. However, the needle portion angle and the frustum portion angle are appropriately determined according to the shape of the needle-like protrusion 112 to be formed.

The needle portion 114 has a bottom surface with a large area and a shape having a narrowest area at the distal end apart from the bottom surface. Since the bottom surface of the needle portion 114 having a large area is connected to the upper bottom surface of the frustum portion 116, the needle portion 114 has a tapered shape in a direction away from the frustum portion 116. The needle-like protrusion 112 constituted by the needle portion 114 and the frustum portion 116 has a tapered shape as a whole from the base portion 102 toward the distal end. The plurality of, for example, 4 to 2500 needle-like protrusions 112 are provided on the base portion 102. However, the number of needle-like protrusions 112 is not limited thereto.

In FIG. 1, the frustum portion 116 has a truncated cone shape, and the needle portion 114 has a cone shape. The shape of the distal end of the needle portion 114 can be appropriately changed to a curved surface having a radius of curvature of 0.01 μm or more and 50 μm or less, a flat surface, or the like according to the degree of insertion of the needle portion 114 into the skin.

Plate Precursor

Figure 2:
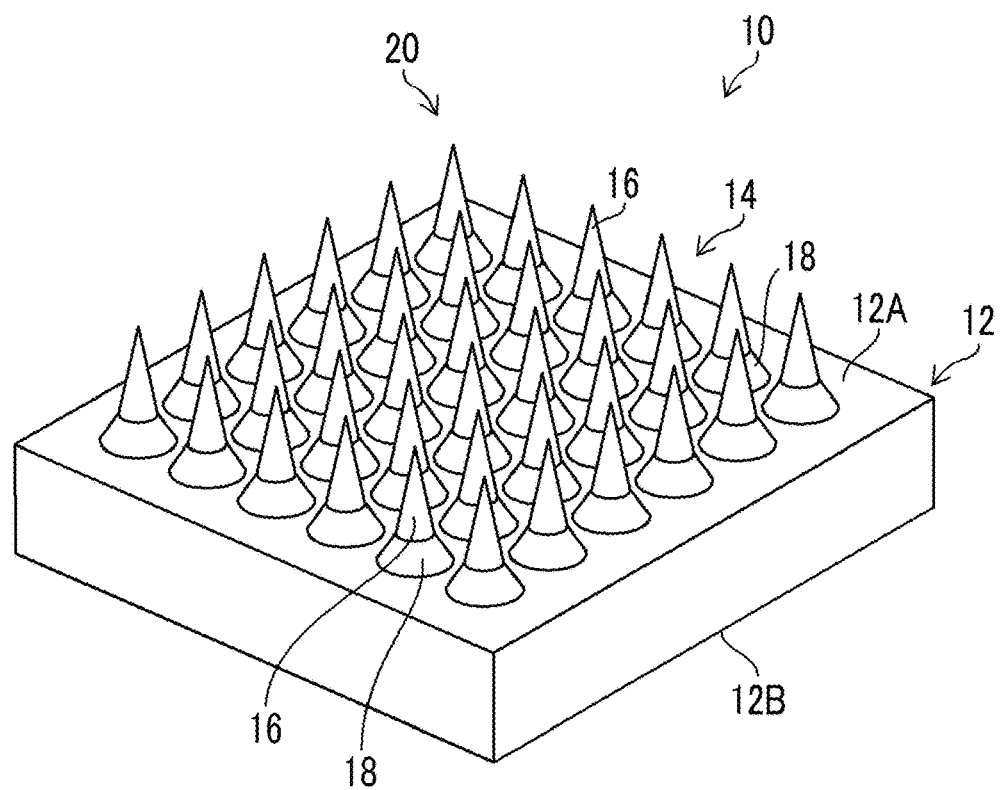
FIG. 2 is a perspective view illustrating an example of a plate precursor having needle-like protrusions.

FIG. 2 is a perspective view of the plate precursor used to manufacture (mold) the microneedle array 100. As illustrated in FIG. 2, a plate precursor 10 has a base portion 12 having a rectangular parallelepiped shape. The base portion 12 has at least a first surface 12A and a second surface 12B which oppose each other. A plurality of needle-like protrusions 14 are provided on the first surface 12A of the base portion 12. The needle-like protrusion 14 includes a needle portion 16 and a frustum portion 18. The needle portion 16 and the frustum portion 18 constituting the needle-like protrusion 14 are arranged in the order of the frustum portion 18 and the needle portion 16 from the base portion 12. The plurality of needle-like protrusions 14 constitute a protruding pattern 20.

The needle-like protrusions 14 of the plate precursor 10 conform to the size, shape, and arrangement of the needle-like protrusions 112 of the microneedle array 100 to be manufactured. Conforming includes a case of substantially conforming. It is important for the manufacturer of the microneedle array 100 to first manufacture the plate precursor 10 having the needle-like protrusions 14 that generally conform to the shape of the needle-like protrusions 112 (microneedles) to be manufactured, within a short period of time.

Manufacturing Method of Plate Precursor

Figure 3:
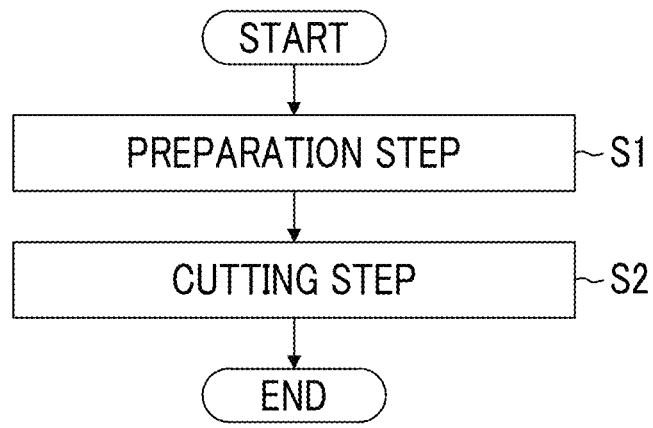
FIG. 3 is a flowchart of a manufacturing method of the plate precursor having needle-like protrusions.

Next, a manufacturing method of the plate precursor 10 having the needle-like protrusions 14 of this embodiment will be described with reference to the drawings. FIG. 3 is a flowchart of the manufacturing method of the plate precursor 10 having the needle-like protrusions 14. As shown in FIG. 3, the manufacturing method of the plate precursor 10 having the needle-like protrusions 14 at least includes a preparation step (step S1) and a cutting step (step S2).

In the preparation step (step S1), a base material and a cutting tool are prepared. In the cutting step (step S2), the base material is cut by rotating and revolving the cutting tool, thereby forming needle-like protrusions. Each step will be described below.

Preparation Step (Step S1)

Figure 4:
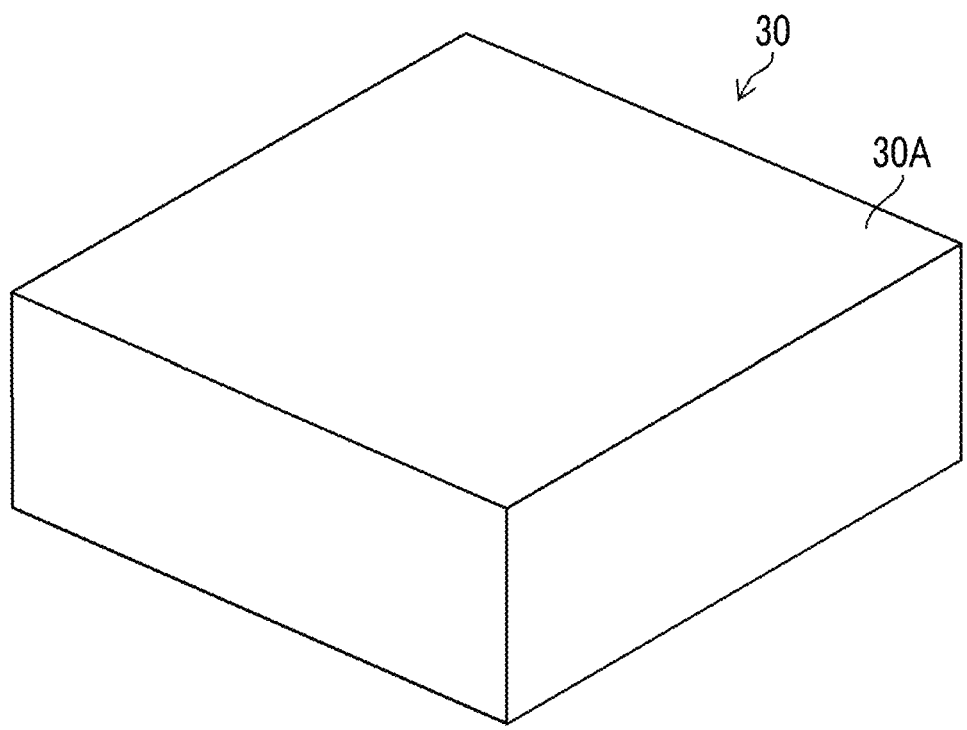
FIG. 4 is a perspective view illustrating an example of a base material.

The preparation step (step S1) will be described based on FIGS. 4 to 7. As illustrated in FIG. 4, the base material for manufacturing the plate precursor 10 (see FIG. 2) having the needle-like protrusions 14 is prepared. A base material 30 has a rectangular parallelepiped shape. The base material 30 has a flat surface 30A to be cut. As a material of the base material 30, metal, cemented carbide, or ceramic can be suitably applied. As the metal, iron, aluminum, stainless steel, Ni plating, Cu plating, brass, titanium, and the like can be suitably applied. However, the material of the base material 30 is not limited to the material.

Figure 5:
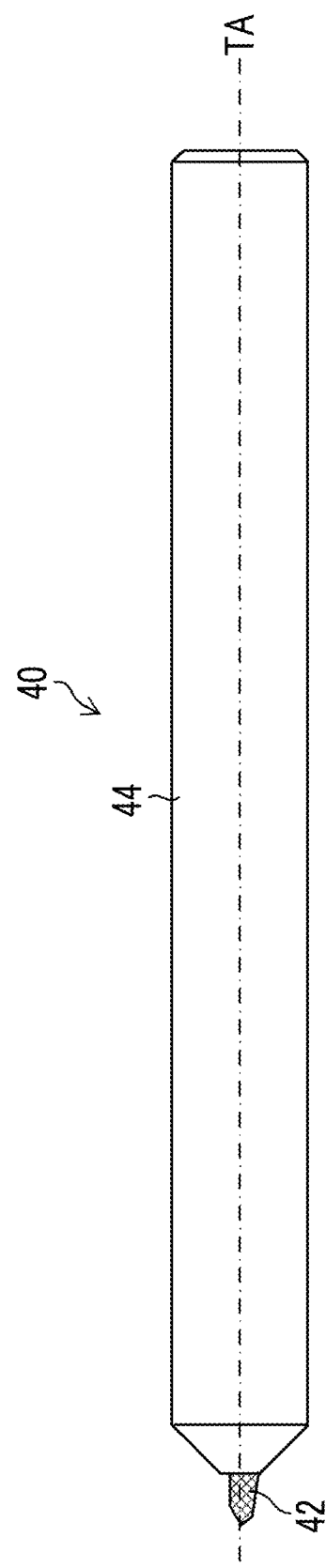
FIG. 5 is a front view of a cutting tool.
Figure 6:
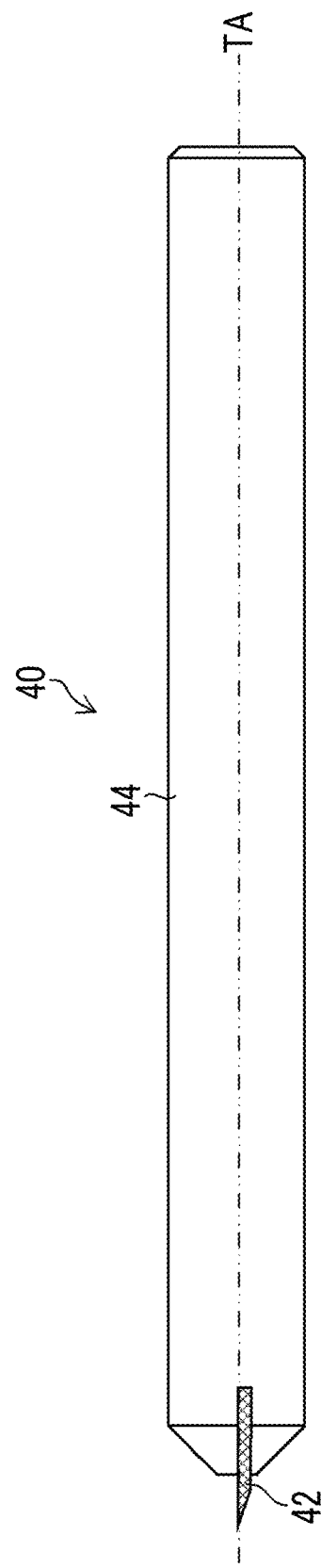
FIG. 6 is a side view of the cutting tool.

As illustrated in FIGS. 5 and 6, the cutting tool is prepared. A cutting tool 40 comprises a blade 42 and a holder 44 that holds the blade 42. The holder 44 is constituted by a portion having a cylindrical shape and a portion having a truncated cone shape, and the blade 42 is held by the truncated cone portion on the distal end of the holder 44. The cutting tool 40 is attached to a spindle (not illustrated) and can rotate about a tool axis TA.

As a material of the cutting tool 40, cemented carbide metal, monocrystalline diamond, polycrystalline diamond, cubic boron nitride (CBN), or sintered diamond (polycrystalline diamond (PCD)) can be suitably applied.

Figure 7:
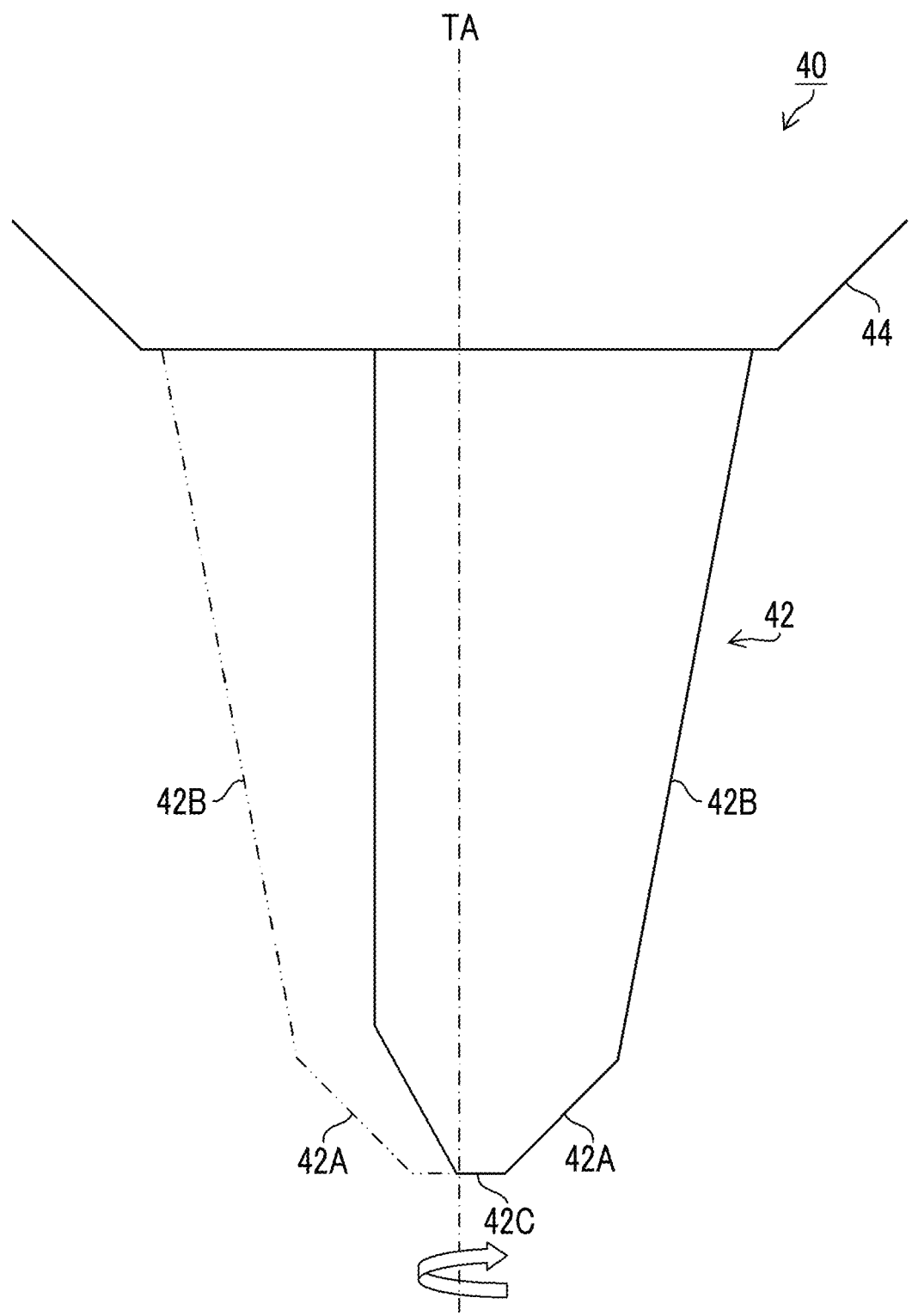
FIG. 7 is a partial enlarged view of the cutting tool in the state of FIG. 5.

FIG. 7 is a partial enlarged view of the cutting tool 40 in the state of FIG. 5. The blade 42 is shown by solid line in FIG. 7. The blade 42 has a shape that conforms to the external shape of the needle-like protrusion 14 (see FIG. 2). As illustrated in FIG. 7, the blade 42 comprises a frustum blade 42A that conforms to the frustum portion 18 of the needle-like protrusion 14 and a needle blade 42B that conforms to the needle portion 16 of the needle-like protrusion 14. The blade 42 has a bottom surface blade 42C at its distal end. The bottom surface blade 42C forms the first surface 12A of the plate precursor 10. The first surface 12A is a reference surface that determines the height of the needle-like protrusions 14. In addition, two-dot chain line indicates the trajectory of the blade 42 in a case where the blade 42 is rotated about the tool axis TA.

Cutting Step (Step S2)

Figure 8:
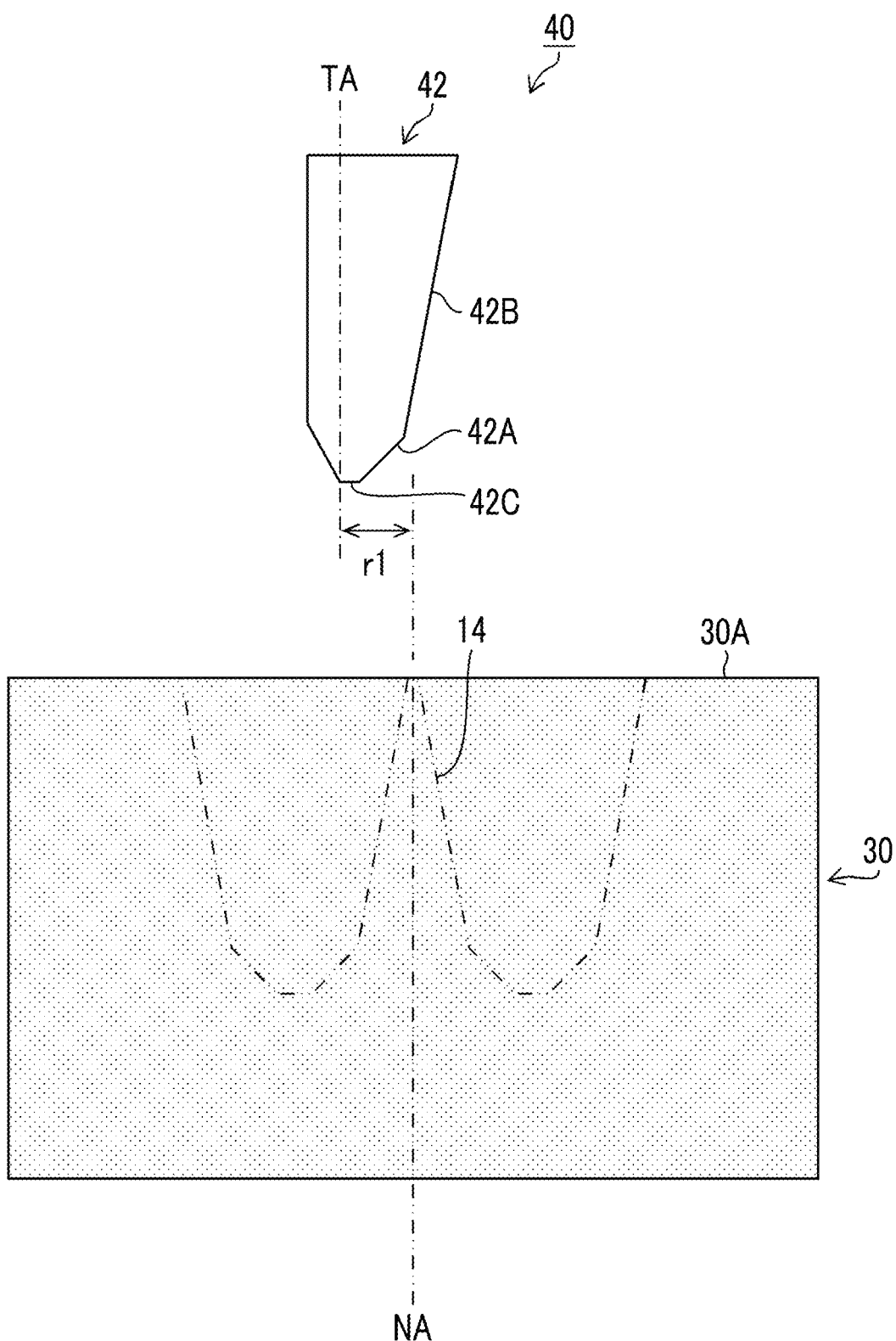
FIG. 8 is a view for describing a preparation step.

A first embodiment of the cutting step (step S2) will be described based on FIGS. 8 to 12. As illustrated in FIG. 8, the cutting tool 40 and the base material 30 are aligned. In the alignment, a distance r1 between the tool axis TA of the cutting tool 40 and an axis NA of the needle-like protrusion 14 to be formed on the base material 30 is adjusted.

Figure 9:
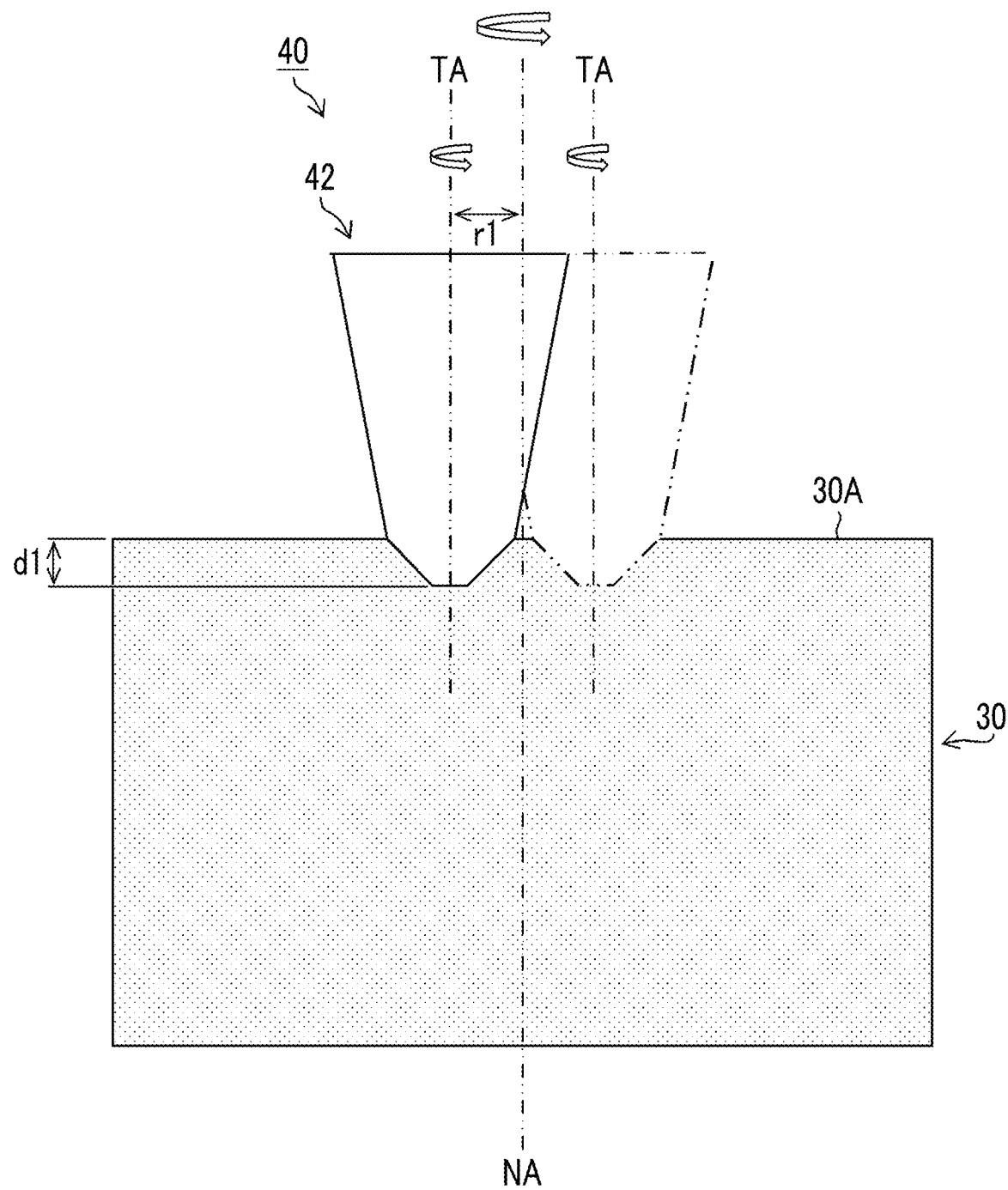
FIG. 9 is a view for describing a cutting step.

As illustrated in FIG. 9, the cutting tool 40 and the base material 30 are moved relative to each other to a position where the cutting tool 40 and the base material 30 come into contact with each other while maintaining a state where the tool axis TA and the axis NA are parallel (or the tool axis TA and the normal to the flat surface 30A are parallel). The cutting tool 40 rotates about the tool axis TA. In addition, the cutting tool 40 revolves around the axis NA, with the distance r1 as the revolution radius. The blade 42 of the cutting tool 40 cuts the flat surface 30A of the base material 30. The cutting tool 40 moves to the inside of the base material 30 to a predetermined depth d1. In FIG. 9, the cutting tool 40 performs machining on the distal end of the needle-like protrusion 14.

Figure 10:
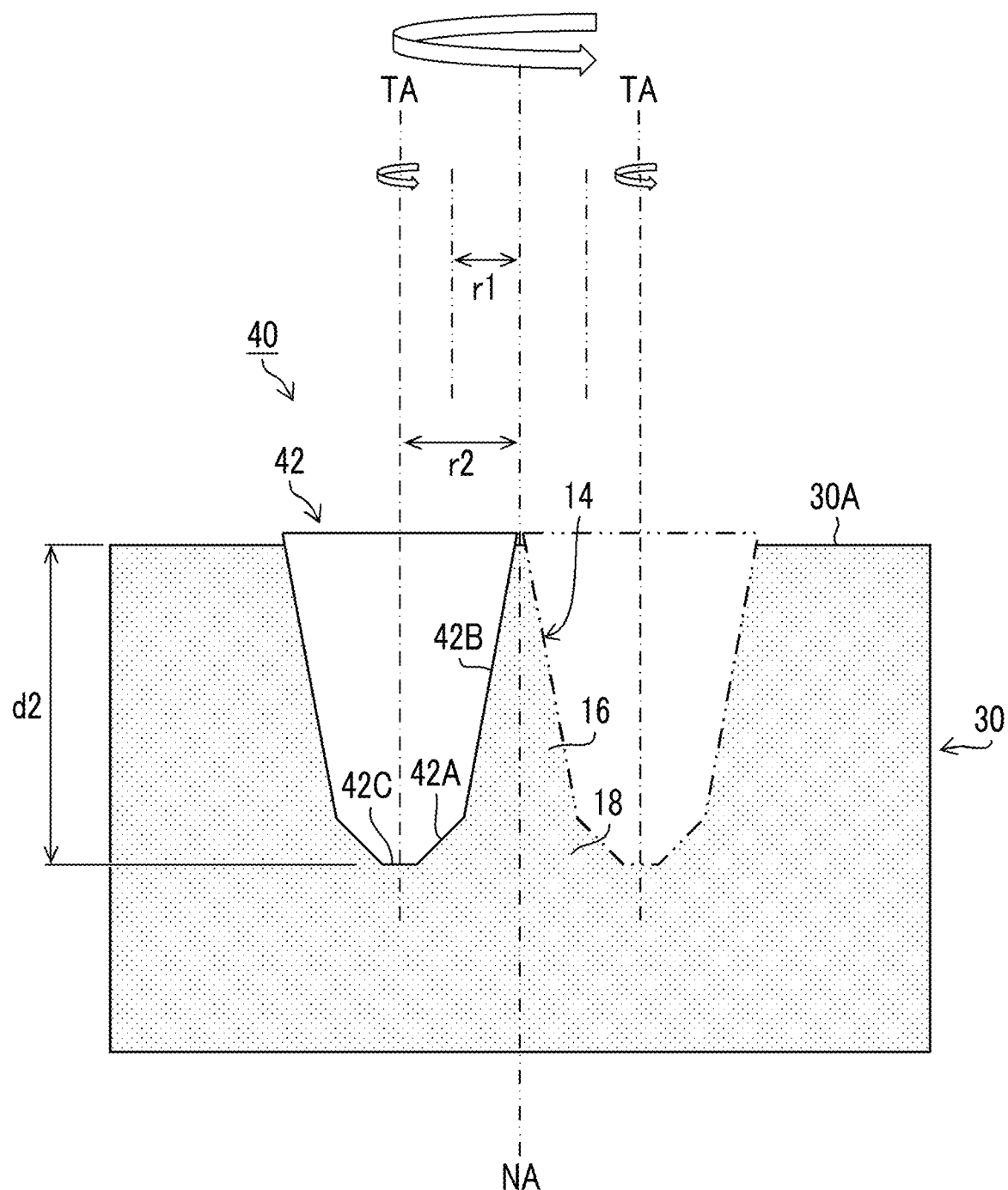
FIG. 10 is a view for describing a cutting step of a first embodiment.

As illustrated in FIG. 10, the cutting tool 40 moves in a direction away from the axis NA until a distance r2 between the tool axis TA and the axis NA is reached. The cutting tool 40 rotates about the tool axis TA. The cutting tool 40 revolves around the axis NA with the distance r2 as the revolution radius. The blade 42 of the cutting tool 40 cuts the inside of the base material 30. The cutting tool 40 moves parallel to the tool axis TA toward the inside of the base material 30 stepwise to a predetermined depth d2 (the height of the needle-like protrusion 14). As illustrated in FIG. 10, the needle-like protrusion 14 having a shape conforming to the shape of the cutting tool 40 is formed. The frustum blade 42A of the blade 42 forms the shape of the frustum portion 18 of the needle-like protrusion 14. The needle blade 42B of the blade 42 forms the shape of the needle portion 16 of the needle-like protrusion 14. The bottom surface blade 42C of the blade 42 forms the shape of the first surface 12A of the plate precursor 10.

In the cutting step of the first embodiment, the cutting tool 40 moves to the inside of the base material 30 spirally, that is, continuously about the axis NA. The cutting tool 40 moves while maintaining the angle of the tool axis TA in a case of contacting the base material 30, that is, moves parallel to the tool axis TA.

Figure 11:
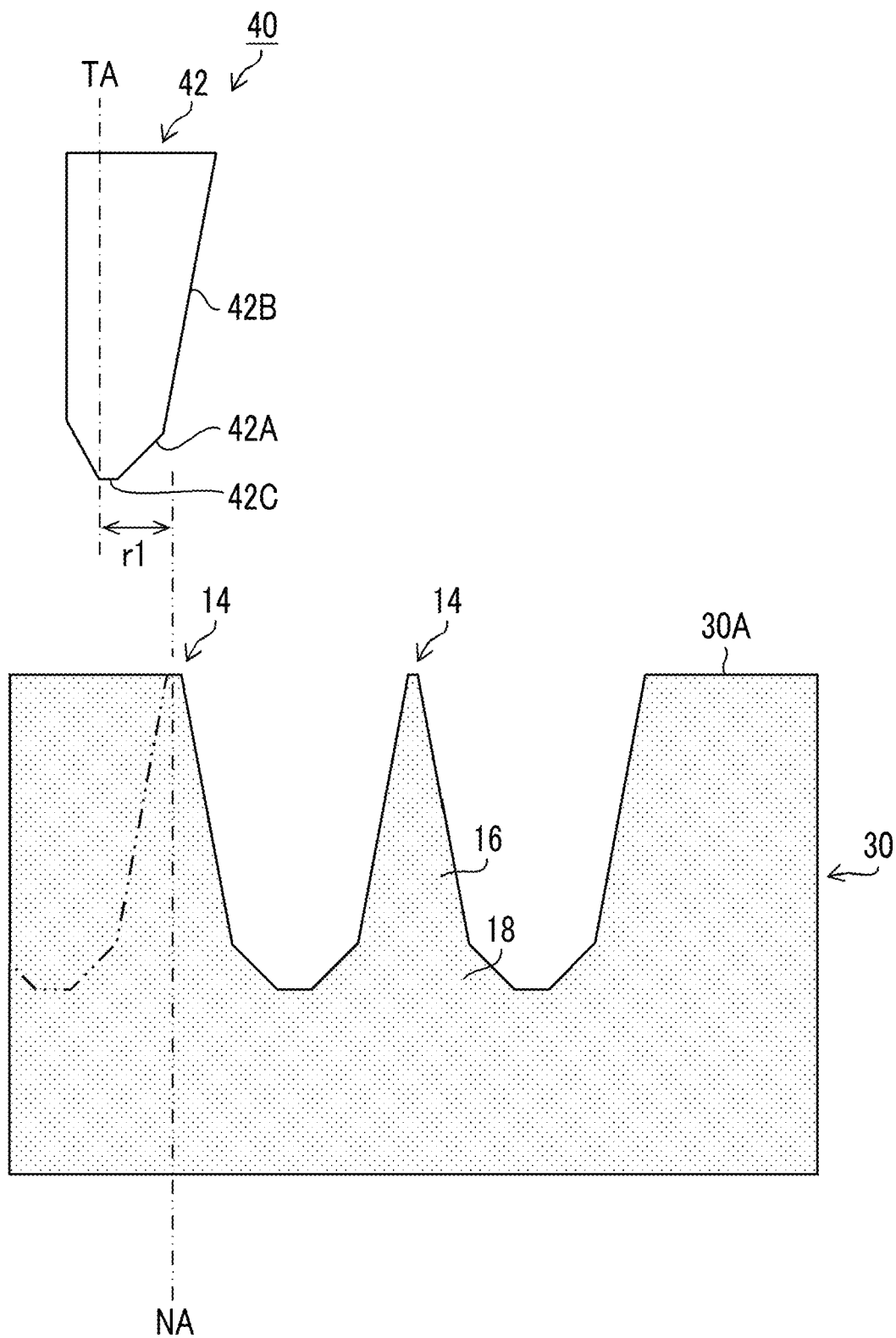
FIG. 11 is a view for describing the cutting step of the first embodiment.

As illustrated in FIG. 11, the cutting tool 40 moves in a direction away from the base material 30 in a case where the formation of the needle-like protrusion 14 is finished. The cutting tool 40 moves to a position where the axis NA of the needle-like protrusion 14 to be formed next and the tool axis TA are at the distance r1. The cutting tool 40 repeats the operations of FIGS. 9 and 10 described above until the required number of needle-like protrusions 14 are formed.

In this embodiment, the use of the cutting tool 40 makes it possible to manufacture the plate precursor 10 having the needle-like protrusions 14 within a short period of time.

Figure 12:
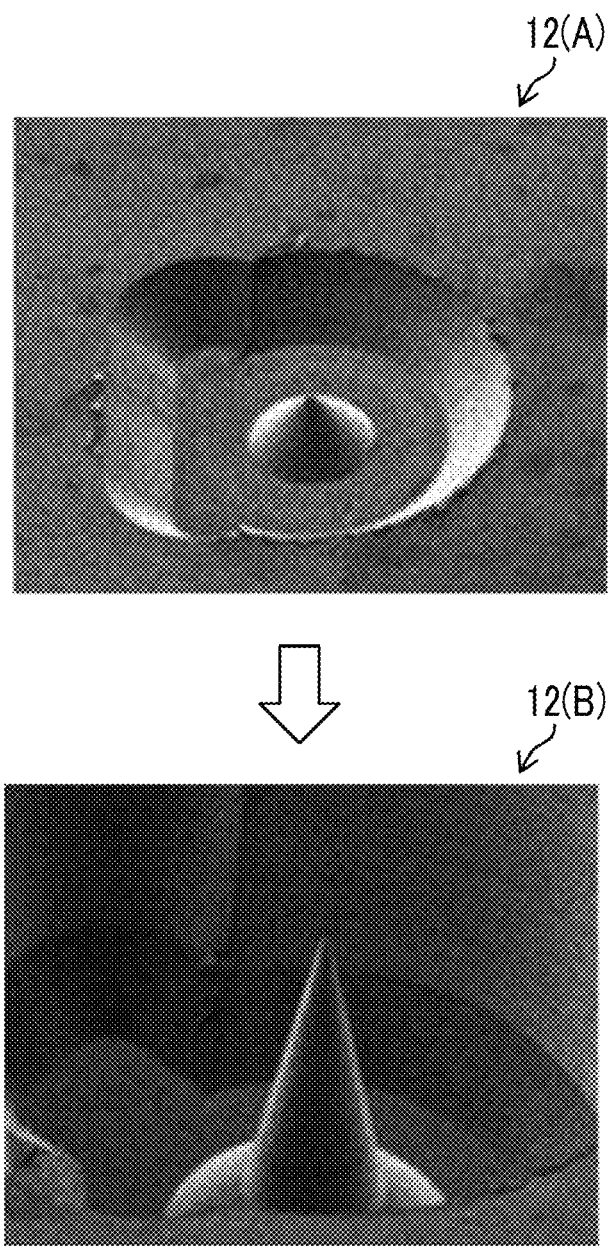
FIG. 12 is a micrograph of needle-like protrusions formed according to the first embodiment.

FIG. 12 is a micrograph showing the cutting step of the needle-like protrusion 14 formed on the base material 30. (A) of FIG. 12 is a micrograph during the formation of the needle-like protrusion. (A) of FIG. 12 corresponds to FIG. 9 described above. (B) of FIG. 12 is a micrograph of the needle-like protrusion. (B) of FIG. 12 corresponds to FIG. 10 described above. As illustrated in FIG. 12, it can be understood that the needle-like protrusion can be formed on the base material by the cutting tool.

Figure 13:
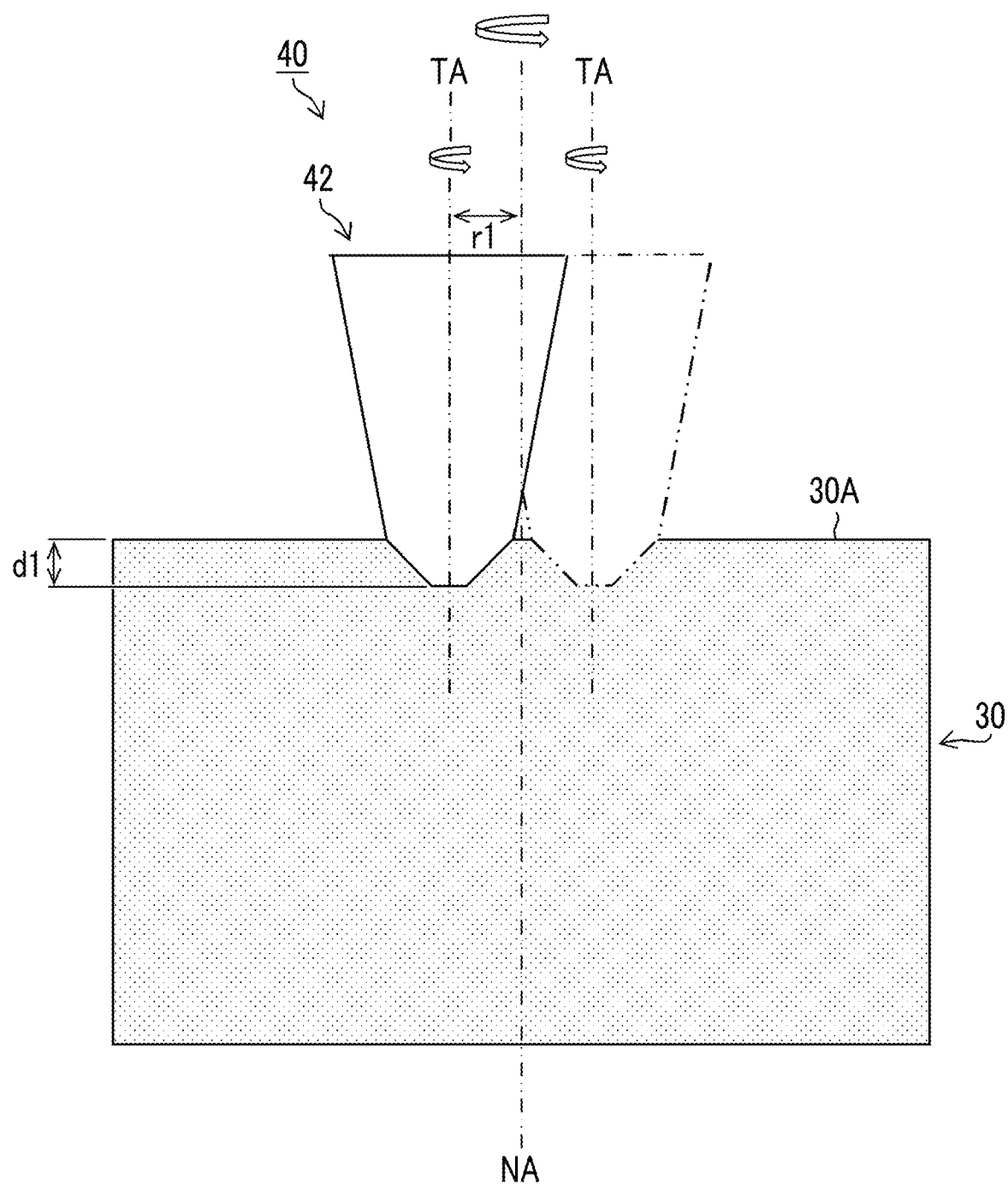
FIG. 13 is a view for describing a cutting step of a second embodiment.

Next, a second embodiment of the cutting step (step S2) will be described based on FIGS. 13 to 17. As illustrated in FIG. 13, after the cutting tool 40 and the base material 30 are aligned, the cutting tool 40 and the base material 30 are moved relative to each other to a position where the cutting tool 40 and the base material 30 come into contact with each other while maintaining a state where the tool axis TA and the axis NA are parallel. The cutting tool 40 rotates about the tool axis TA. In addition, the cutting tool 40 revolves around the axis NA, with the distance r1 as the revolution radius. The blade 42 of the cutting tool 40 cuts the flat surface 30A of the base material 30. The cutting tool 40 moves to the inside of the base material 30 to a predetermined depth d1. FIG. 13 of the second embodiment is the same as FIG. 9 of the first embodiment.

Figure 14:
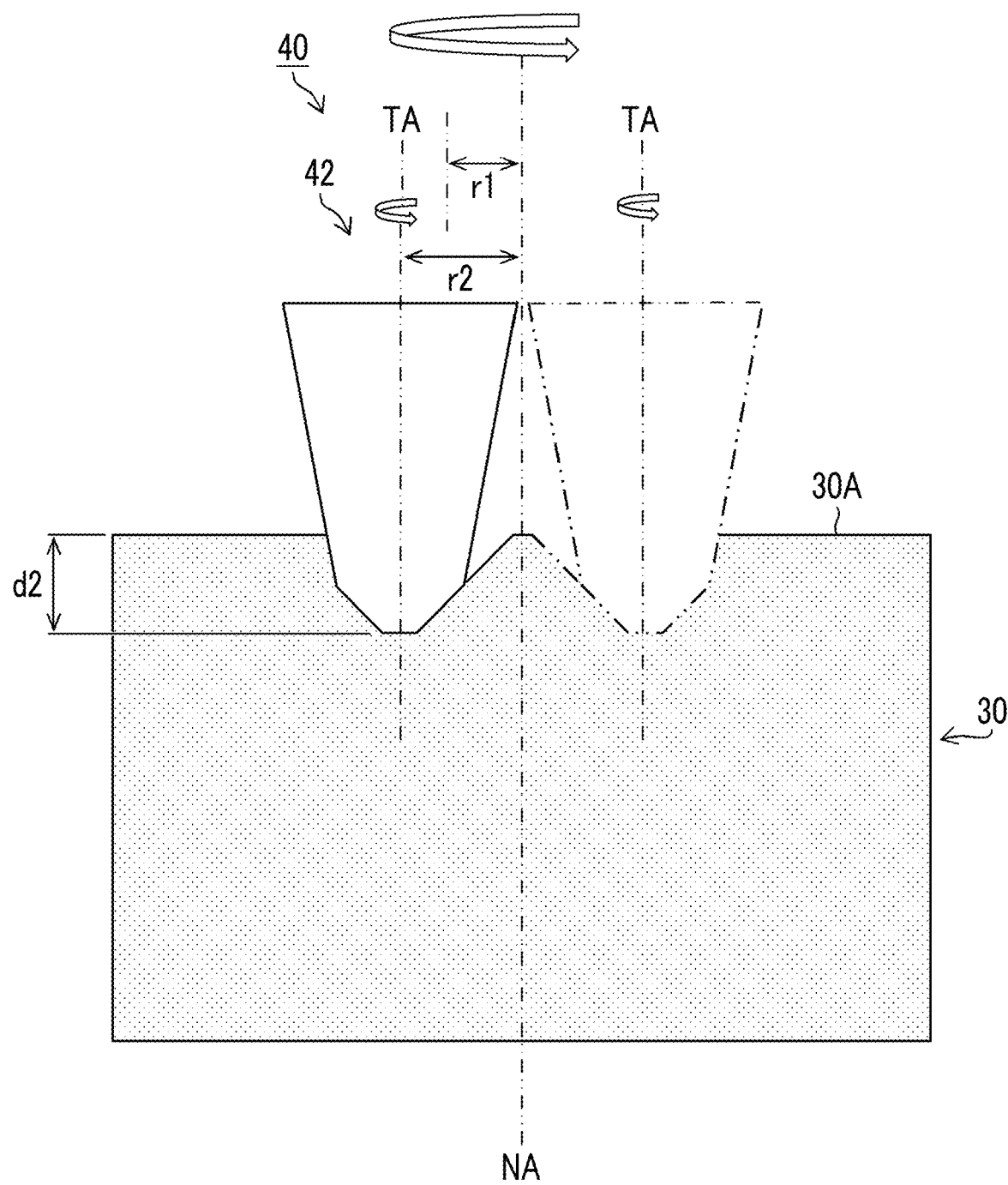
FIG. 14 is a view for describing the cutting step of the second embodiment.

As illustrated in FIG. 14, the cutting tool 40 moves in a direction away from the axis NA until the distance r2 between the tool axis TA and the axis NA is reached. The cutting tool 40 rotates about the tool axis TA. The cutting tool 40 moves linearly to the inside of the base material 30 from the depth d1 to the predetermined depth d2. The cutting tool 40 moves to the inside of the base material 30 stepwise to the depth d2. The depth d2 is less than the height of the needle-like protrusion 14.

At the position of the depth d2, the cutting tool 40 revolves around the axis NA with the distance r2 as the revolution radius. The blade 42 of the cutting tool 40 cuts the inside of the base material 30. In FIG. 14, the cutting tool 40 stops moving to the inside of the base material 30 at the depth d2.

Figure 15:
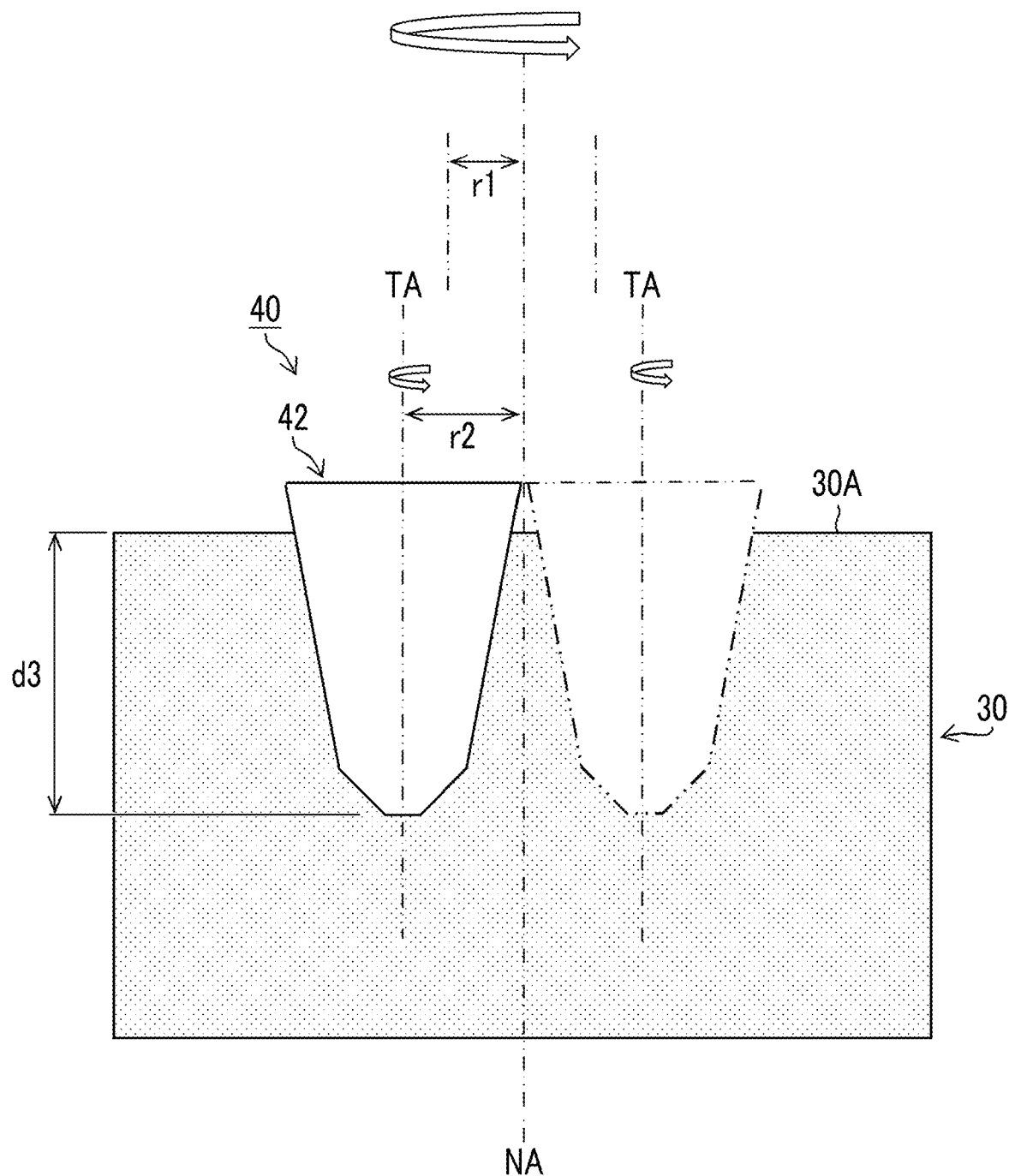
FIG. 15 is a view for describing the cutting step of the second embodiment.

As illustrated in FIG. 15, the cutting tool 40 moves linearly to the inside of the base material 30 from the depth d2 to a predetermined depth d3. The cutting tool 40 moves to the inside of the base material 30 stepwise to the depth d3. The depth d3 is less than the height of the needle-like protrusion 14.

At the position of the depth d3, the cutting tool 40 revolves around the axis NA with the distance r2 as the revolution radius. The blade 42 of the cutting tool 40 cuts the inside of the base material 30. In FIG. 15, the cutting tool 40 stops moving to the inside of the base material 30 at the depth d3.

Figure 16:
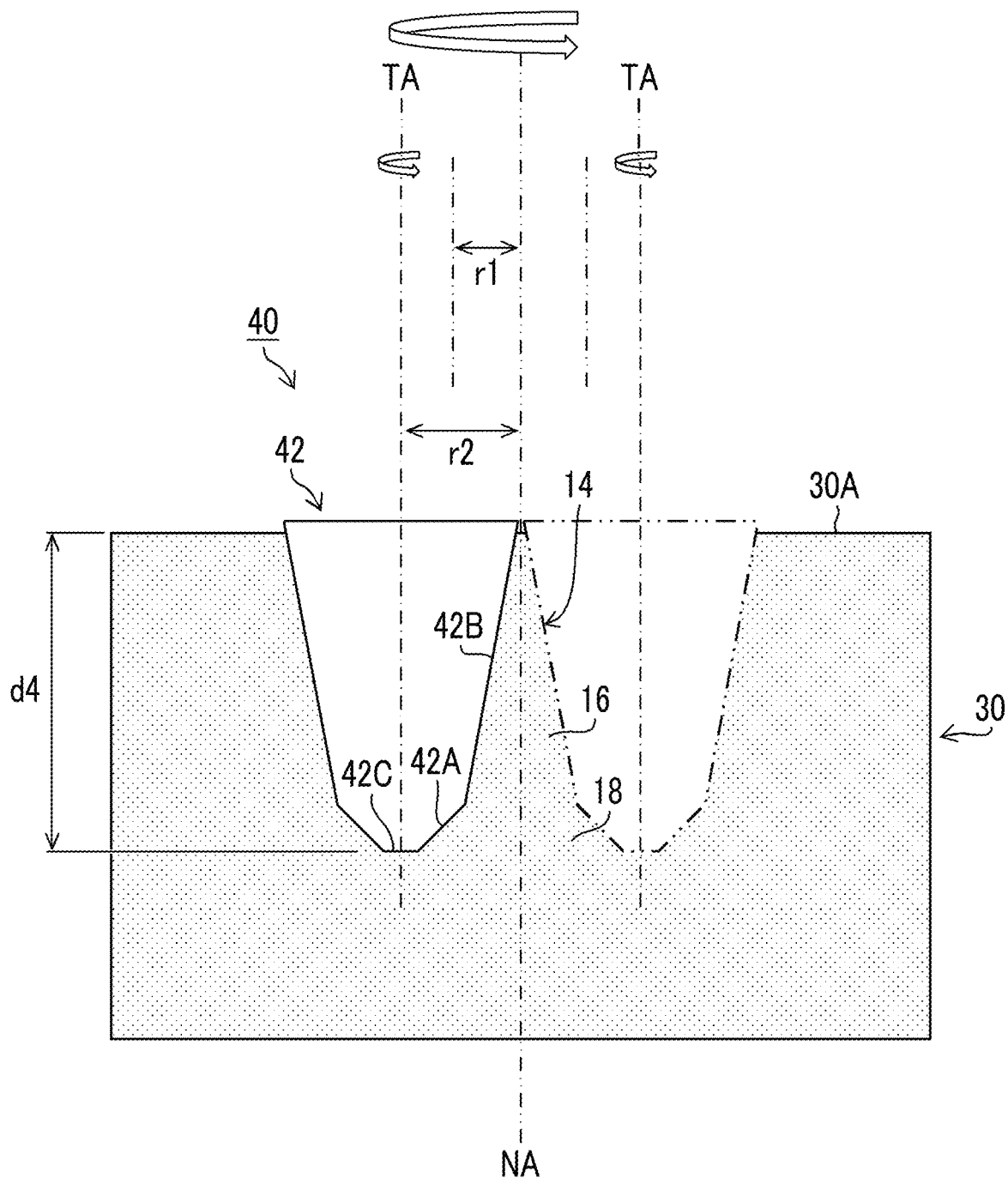
FIG. 16 is a view for describing the cutting step of the second embodiment.

As illustrated in FIG. 16, the cutting tool 40 moves linearly to the inside of the base material 30 from the depth d3 to a predetermined depth d4. The cutting tool 40 moves to the inside of the base material 30 stepwise to the depth d4. The depth d4 is coincident with the height of the needle-like protrusion 14.

At the position of the depth d4, the cutting tool 40 revolves around the axis NA with the distance r2 as the revolution radius. The blade 42 of the cutting tool 40 cuts the inside of the base material 30.

As illustrated in FIG. 16, the needle-like protrusion 14 having a shape conforming to the shape of the cutting tool 40 is formed. The frustum blade 42A of the blade 42 forms the shape of the frustum portion 18 of the needle-like protrusion 14. The needle blade 42B of the blade 42 forms the shape of the needle portion 16 of the needle-like protrusion 14. The bottom surface blade 42C of the blade 42 forms the shape of the first surface 12A of the plate precursor 10.

In the cutting step of the second embodiment, the stepwise movement of the cutting tool 40 is an intermittent movement. The intermittent movement of the cutting tool 40 can suppress the deformation of the needle-like protrusion 14 during cutting.

Figure 17:
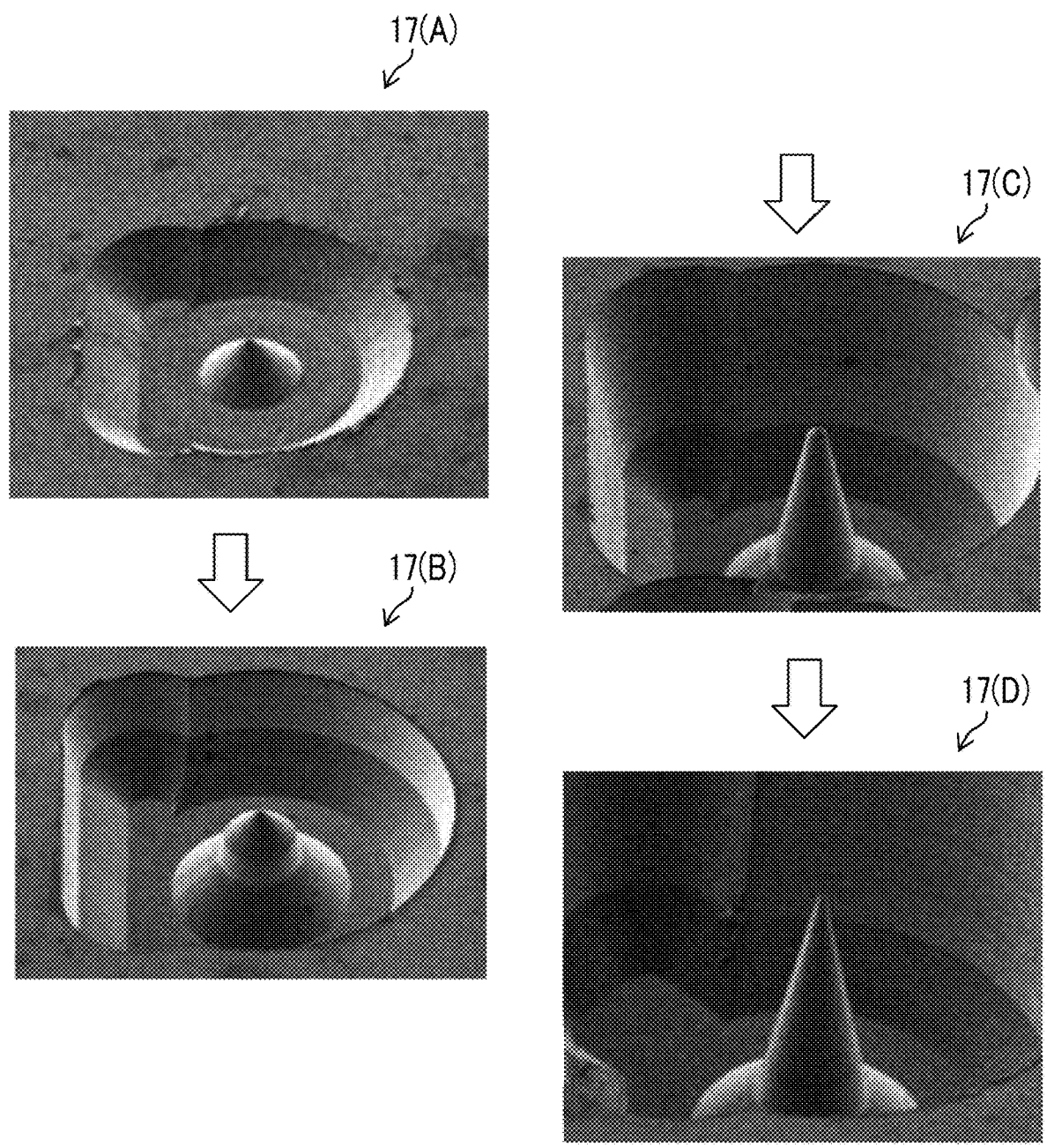
FIG. 17 is a micrograph of needle-like protrusions formed according to the second embodiment.

FIG. 17 is a micrograph showing the cutting step of the needle-like protrusion formed on the base material. (A) of FIG. 17, (B) of FIG. 17, and (C) of FIG. 17 are micrographs during the formation of the needle-like protrusion. (A) of FIG. 17 corresponds to FIG. 13 described above. (B) of FIG. 17 corresponds to FIG. 14 described above. (C) of FIG. 17 corresponds to FIG. 15 described above. (D) of FIG. 17 is a micrograph of the needle-like protrusion. (D) of FIG. 17 corresponds to FIG. 16 described above. As illustrated in FIG. 17, it can be understood that the needle-like protrusion can be formed on the base material by the cutting tool.

Figure 18:
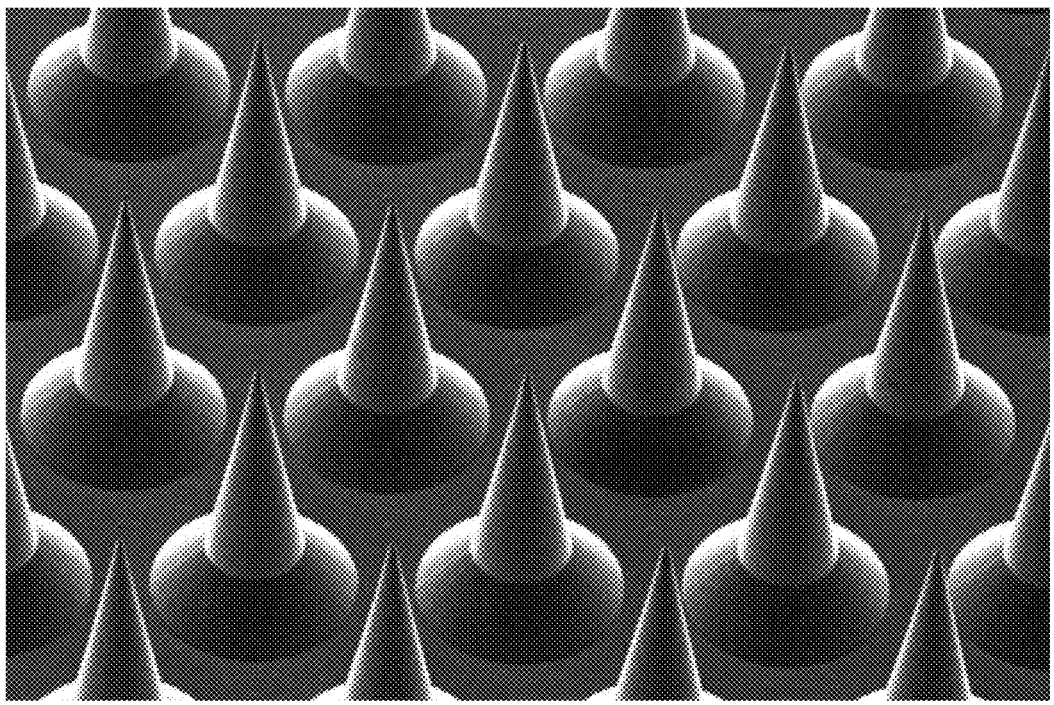
FIG. 18 is a micrograph of a plurality of needle-like protrusions.

FIG. 18 is a micrograph of a plurality of the needle-like protrusions 14 formed on the base material. The plurality of needle-like protrusions can be formed by repeating the above-described cutting step (step S2) a plurality of times. The use of the cutting tool makes it possible to manufacture the plate precursor having the plurality of needle-like protrusions within a short period of time. The needle-like protrusion has the frustum portion conforming to the frustum portion of the blade and the needle portion conforming to the needle blade of the blade. The first surface of the base portion excluding the needle-like protrusion is machined flat so as to conform to the bottom surface blade of the blade.

Figure 19:
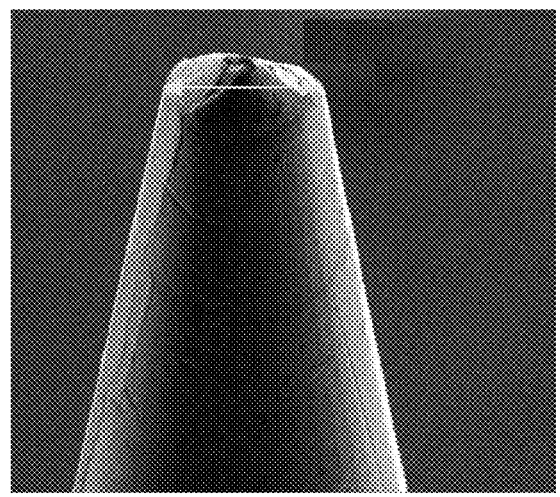
FIG. 19 is an enlarged micrograph of the distal end of the needle-like protrusion.
Figure 20:
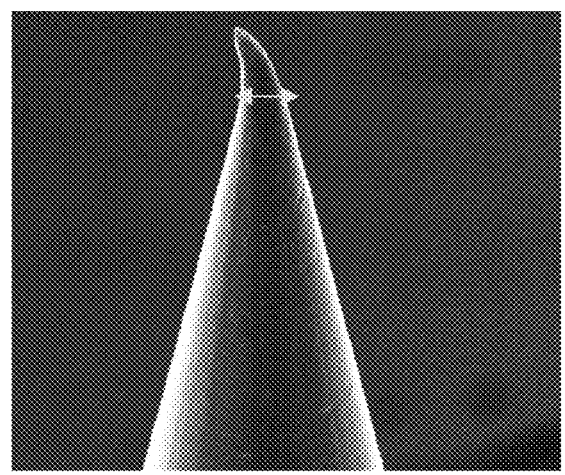
FIG. 20 is an enlarged micrograph of the distal end of the needle-like protrusion.
Figure 21:
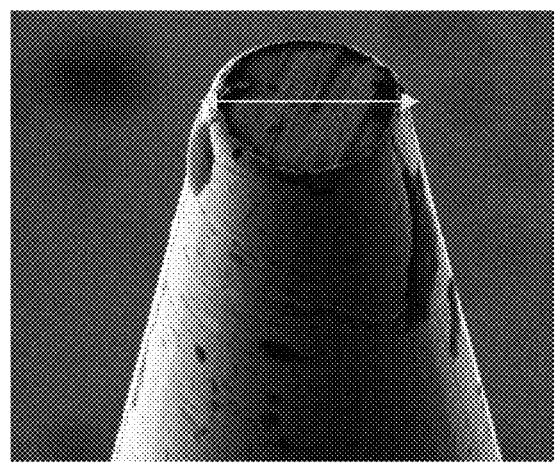
FIG. 21 is an enlarged micrograph of the distal end of the needle-like protrusion.

FIGS. 19 to 21 are enlarged micrographs of the distal end of the needle-like protrusion. FIG. 19 is an enlarged photograph of the distal end of the needle-like protrusion which is cut with the distance r2 (see FIGS. 10 and 14 to 16) between the tool axis TA and the axis NA as the revolution radius. FIG. 20 is an enlarged photograph of the distal end of the needle-like protrusion which is cut with a revolution radius shorter than the distance r2 compared to FIG. 19. FIG. 21 is an enlarged photograph of the distal end of the needle-like protrusion which is cut with a revolution radius longer than the distance r2 compared to FIG. 19. The diameter of the distal end of the needle-like protrusion increases in the order of FIG. 20, FIG. 19, and FIG. 21. As illustrated in FIGS. 19 to 21, it can be understood that the shape of the needle-like protrusion can be controlled by adjusting the distance between the tool axis TA and the axis NA.

Figure 22:
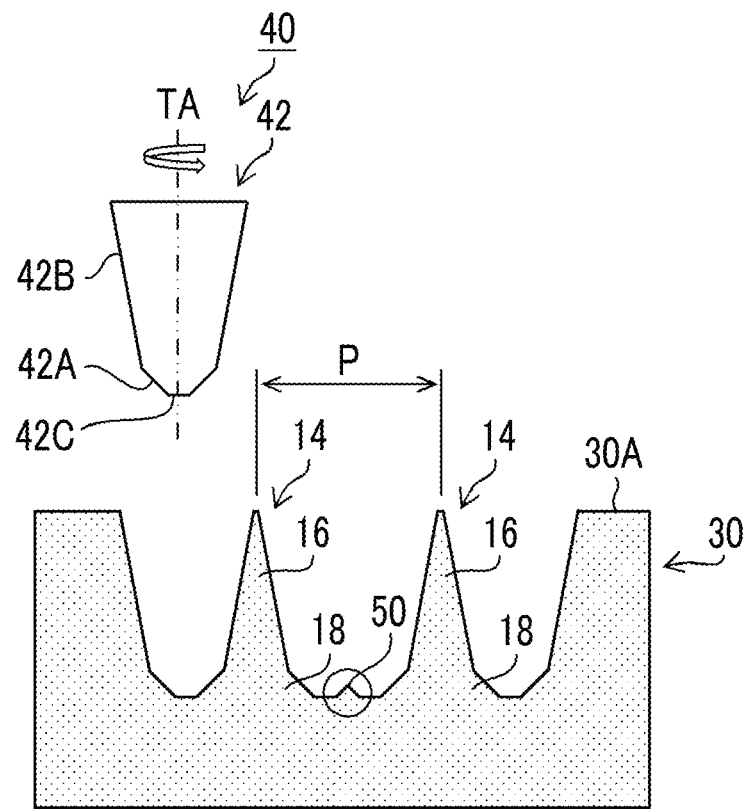
FIG. 22 is an explanatory view for describing an uncut residue of the base material.

Next, a case where an uncut residue occurs on the base material will be described with reference to FIG. 22. As illustrated in FIG. 22, the cutting tools 40 form the needle-like protrusions 14 one by one. In a case where a pitch P of the adjacent needle-like protrusions 14 is large compared to the rotation trajectory of the blade 42, an uncut residue 50 is formed at a position deviating from the trajectory of the cutting tool 40 as indicated by surrounding circle symbol. The uncut residue 50 affects the shape of the microneedle array 100 (see FIG. 1) to be manufactured.

Figure 23:
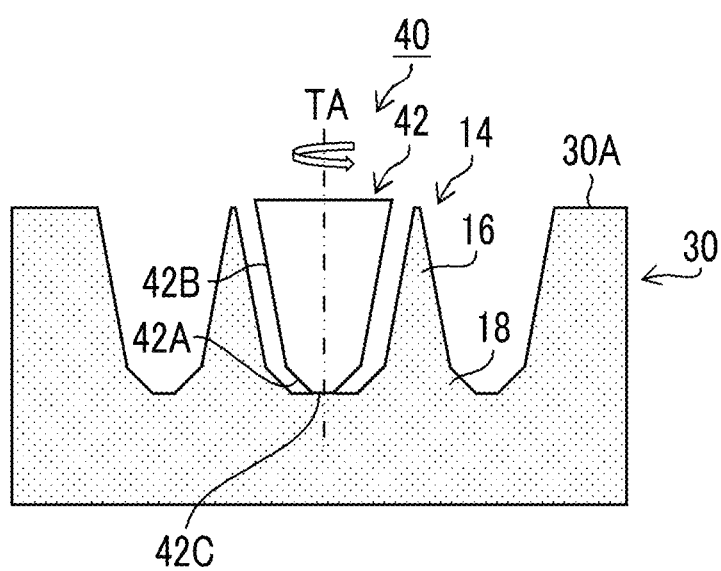
FIG. 23 is an explanatory view for describing a step of cutting the uncut residue.

As illustrated in FIG. 23, the cutting tool 40 is moved between the needle-like protrusions 14, and then the bottom surface blade 42C of the cutting tool 40 cuts the uncut residue 50. The first surface 12A of the base portion 12 of the plate precursor 10 is machined flat.

In addition, the blade 42 of the cutting tool 40 is not limited to the above-described structure. As illustrated in FIG. 24, the cutting tool 40 can comprise a plurality of blades 42. (A) of FIG. 24 illustrates a cutting tool 40 with two blades. In (A) of FIG. 24, the two blades 42 are held by the holder 44. (B) of FIG. 24 illustrates a cutting tool 40 with three blades. In (B) of FIG. 24, the three blades 42 are held by the holder 44. (C) of FIG. 24 illustrates a cutting tool 40 with four blades. In (C) of FIG. 24, the four blades 42 are held by the holder 44. The cutting tool is selected according to the shape of the needle-like protrusion to be manufactured.

Figure 25:
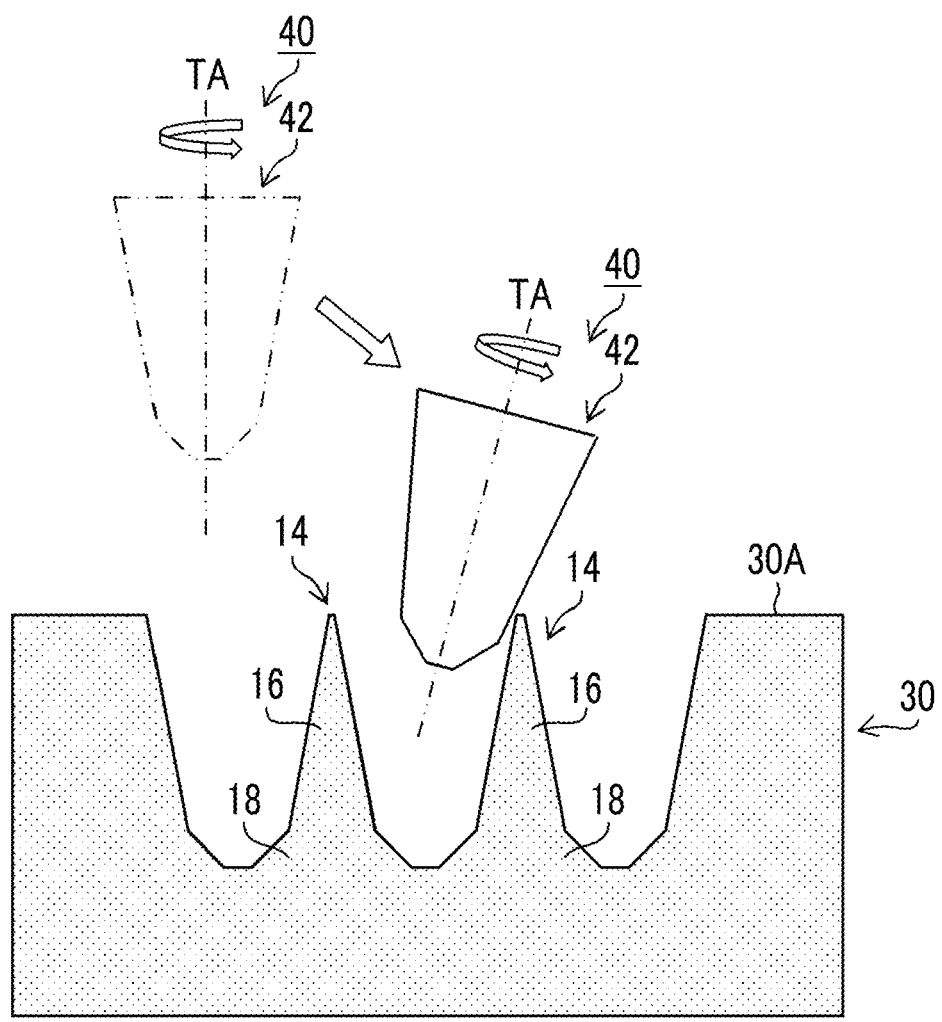
FIG. 25 is a view for describing a first posture and a second posture of the cutting tool.

Next, the posture of the cutting tool will be described with reference to FIG. 25. As illustrated in FIG. 25, by inclining the tool axis TA, a first posture of the cutting tool 40 indicated by two-dot chain line changes to a second posture of the cutting tool 40 indicated by solid line. The cutting tool 40 in the second posture cuts the base material 30. The change in the posture of the cutting tool 40 improves the degree of freedom of cutting and makes it possible to manufacture needle-like protrusions having a more preferable shape.

The conditions for cutting the base material by the cutting tool are appropriately set from, for example, a feed rate of 1 mm/min to 500 mm/min, a cutting depth of 0.01 mm to 2 mm, and a rotational speed of 1000 rpm to 80,000 rpm. However, the cutting conditions are not limited thereto.

Manufacturing Method of Microneedle Array

Next, a manufacturing method of a first microneedle array using the plate precursor manufactured by the above-described manufacturing method will be described.

Figure 26:
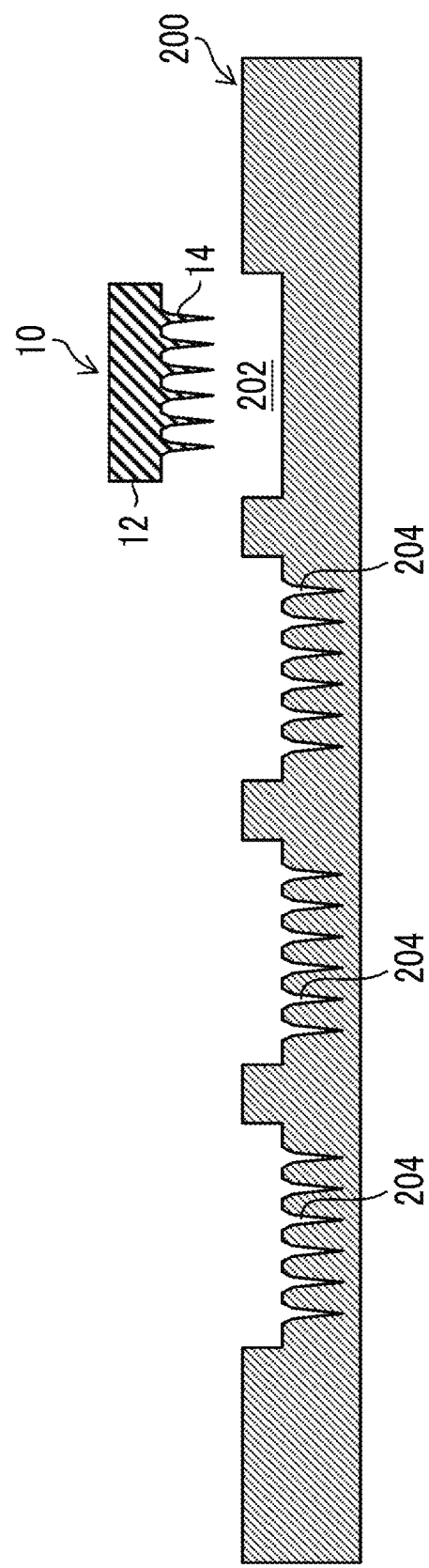
FIG. 26 is a view for describing a step of a manufacturing method of a first microneedle array.

As illustrated in FIG. 26, the plate precursor 10 manufactured by the above-described manufacturing method is prepared. The plate precursor 10 has a size corresponding to one patch of a microneedle array. The plate precursor 10 has the base portion 12 and the plurality of needle-like protrusions 14. The needle-like protrusion 14 has the frustum portion 18 and the needle portion 16. The plate precursor 10 is pressed against a resin precursor 200 having a plurality of recessed portions 202 by an imprint method. A plurality of needle-like recessed portions 204 which are inverted shapes of the needle-like protrusions 14 of the plate precursor 10 are formed in the resin precursor 200. In the imprint method, the plate precursor 10 which is heated is pressed against the resin precursor 200. Next, the plate precursor 10 is separated from the resin precursor 200. The resin precursor 200 is cooled, and the needle-like recessed portions 204 are formed.

Figure 27:
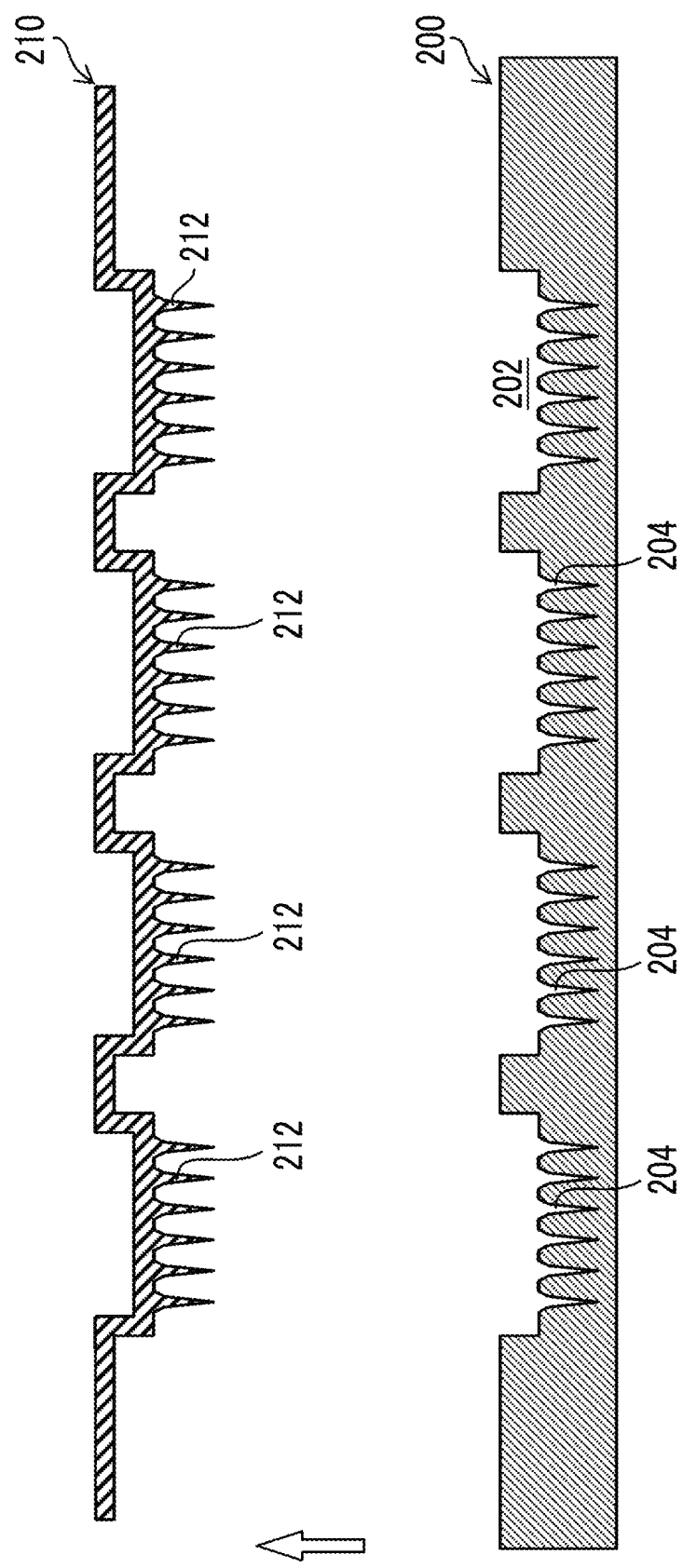
FIG. 27 is a view for describing a step of the manufacturing method of a first microneedle array.

Next, as illustrated in FIG. 27, from the resin precursor 200 having the needle-like recessed portions 204, a duplicate mold 210 having a plurality of needle-like protrusions 212 is produced by electroforming.

In the electroforming, the resin precursor 200 is subjected to a conduction treatment. A metal (for example, nickel) is sputtered onto the resin precursor 200, and the metal adheres to the surface of the resin precursor 200 and the needle-like recessed portions 204.

Next, the resin precursor 200 subjected to the conduction treatment is held by the cathode of an electroforming apparatus (not illustrated). A metal case holding metal pellets is the anode. The cathode holding the resin precursor 200 and the anode holding the metal pellets are immersed in an electroforming liquid. Next, by energization, the metal is embedded in the needle-like recessed portions 204 of the resin precursor 200. The duplicate mold 210 having the plurality of needle-like protrusions 212 is produced by being peeled off from the resin precursor 200.

Figure 28:
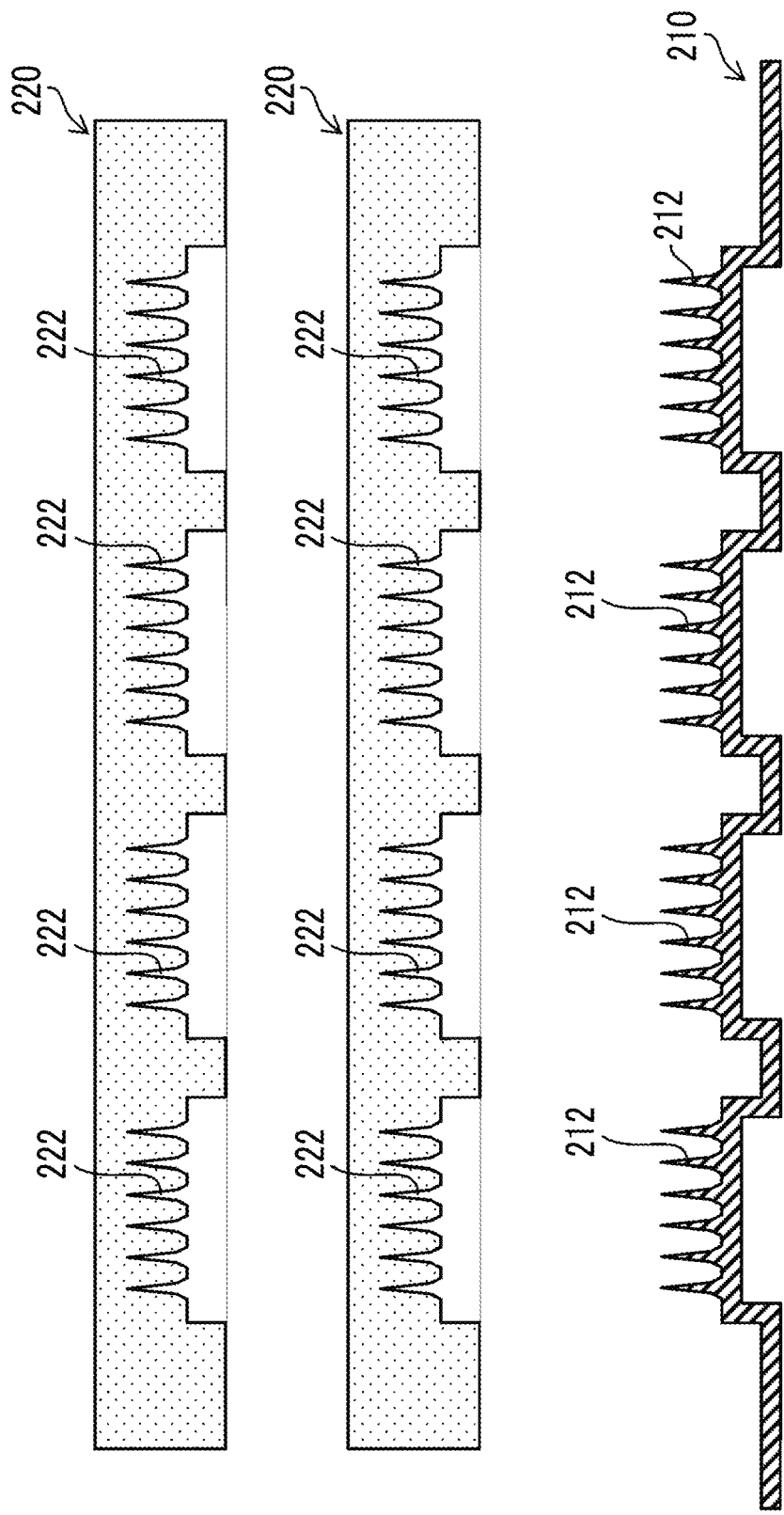
FIG. 28 is a view for describing a step of the manufacturing method of a first microneedle array.

Next, as illustrated in FIG. 28, a resin mold 220 having a plurality of needle-like recessed portions 222 is produced from the duplicate mold 210. The resin mold 220 can be produced, for example, by pouring a medical grade silicone material (for example, MDX4-4210 manufactured by Dow Corning) into the duplicate mold 210, performing a heating treatment thereon at 150° C. so as to be cured, and thereafter peeling off the resin mold 220 from the duplicate mold 210.

As another method, the resin mold 220 can be produced by pouring a UV-curable resin, which is cured by being irradiated with ultraviolet light, into the duplicate mold 210, and irradiating the UV-curable resin with ultraviolet light in a nitrogen atmosphere, and thereafter peeling off the resin mold 220 from the duplicate mold 210.

Furthermore, as still another method, the resin mold 220 can be produced by pouring a plastic resin such as polystyrene and polymethyl methacrylate (PMMA) dissolved in an organic solvent into the duplicate mold 210 coated with a release agent, drying and curing the resultant by volatilizing the organic solvent, and thereafter peeling off the resin mold 220 from the duplicate mold 210. Therefore, the resin mold 220 having the plurality of needle-like recessed portions 222 corresponding to the plurality of needle-like protrusions 212 of the duplicate mold 210 is produced.

Figure 29:
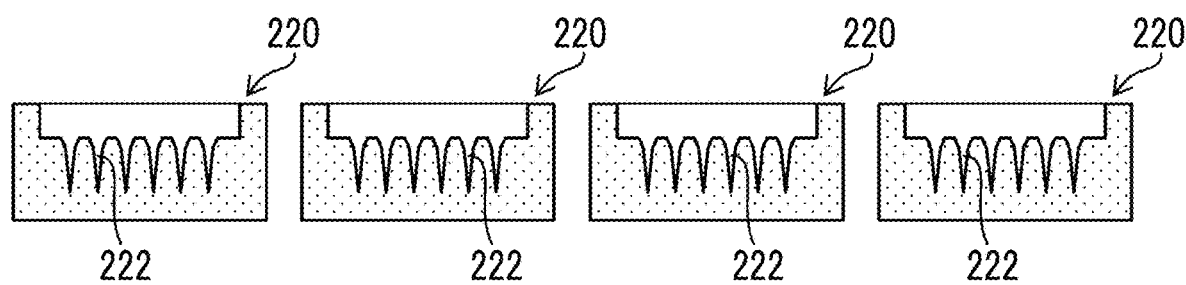
FIG. 29 is a view for describing a step of the manufacturing method of a first microneedle array.

Next, as illustrated in FIG. 29, the resin mold 220 is cut for each of the plurality of needle-like recessed portions 222 corresponding to one patch of the microneedle array. The needle-like recessed portion 222 of the resin mold 220 is an inverted mold of the needle-like protrusion 14 (not illustrated) of the plate precursor 10.

Figure 30:
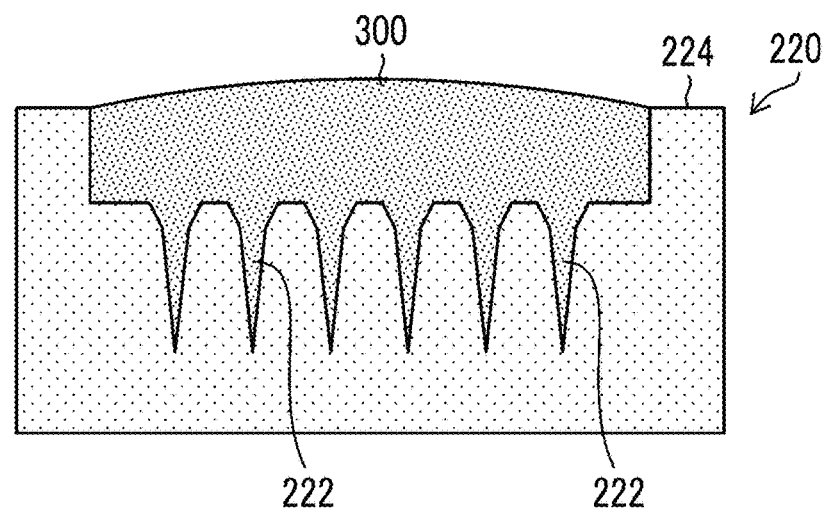
FIG. 30 is a view for describing a step of the manufacturing method of a first microneedle array.

As illustrated in FIG. 30, a liquid material 300 is supplied to the resin mold 220. The liquid material 300 is repelled by a stepped portion 224 of the resin mold 220 and is shrunk by surface tension. The liquid material 300 is fixed (also referred to as pinned) at the corner on the inner diameter side of the stepped portion 224. In order to fill the needle-like recessed portion 222 with the liquid material 300, suction is preferably performed from the side opposite to the side on which the liquid material 300 is placed.

As illustrated in FIG. 31, the liquid material 300 (not illustrated) is dried, and the microneedle array 100 is formed on the resin mold 220. In FIG. 31, since the liquid material 300 is fixed to the corner, the microneedle array 100 having a desired shape can be formed even after drying.

As illustrated in FIG. 32, the microneedle array 100 is separated from the resin mold 220. The separation method is not particularly limited. For example, the microneedle array 100 is separated from the resin mold 220 by adsorbing the second surface 102B of the microneedle array 100 with a suction pad (not illustrated) and moving the suction pad in a direction away from the resin mold 220.

In the embodiment, the case where the microneedle array 100 is formed by filling the needle-like recessed portion 222 by supplying the liquid material 300 to a region surrounded by the stepped portion 224 of the resin mold 220, and drying the resultant is described, but is not limited thereto.

For example, a drug layer can be formed on the distal end side of the needle-like recessed portion 222 before the liquid material 300 is supplied. After the formation of the drug layer, the liquid material 300 containing no drug can be supplied and dried to manufacture the microneedle array 100 having the two-layer structure. The solidified drug layer can suppress diffusion of the drug layer to the liquid material 300.

A polymer solution is preferable as the liquid material 300. As the material of the polymer solution, it is preferable to use a water-soluble material. As a material of a resin polymer of the polymer solution, it is preferable to use a biocompatible resin. As such resins, sugars such as glucose, maltose, pullulan, sodium chondroitin sulfate, sodium hyaluronate, and hydroxyethyl starch, proteins such as gelatin, and biodegradable polymers such as polylactic acid and a lactic acid-glycolic acid copolymer are preferably used. In a case where the microneedle array 100 is released from the resin mold 220, since the microneedle array 100 can be released using the base material (not illustrated), such resins can be suitably used. Although a concentration varies depending on the material, it is preferable that the concentration is set so that the resin polymer is contained at 10 to 50 mass % in the polymer solution which does not contain a drug. A solvent used in the polymer solution may be water or may be volatile, and alcohol such as ethanol or the like may be used.

The above-mentioned polymer solution containing a predetermined amount of drug can be applied as the liquid material for forming the drug layer. Whether or not a predetermined amount of drug is contained is determined by whether or not the drug effect can be exhibited in a case where the body surface is punctured. Therefore, containing a predetermined amount of drug means containing a drug in an amount that exhibits the drug effect in a case where the body surface is punctured.

The drug is not limited as long as the drug has a function as a drug. In particular, the drug is preferably selected from peptides, proteins, nucleic acids, polysaccharides, vaccines, pharmaceutical compounds that belong to a water-soluble low molecular weight compound, or cosmetic ingredients.

Next, a manufacturing method of a second microneedle array using the plate precursor manufactured by the above-described manufacturing method will be described. The manufacturing method of the second microneedle array is different from the manufacturing method of the first microneedle array in that a resin mold is produced from a plate precursor. Hereinafter, only the differences will be described below.

Figure 33:
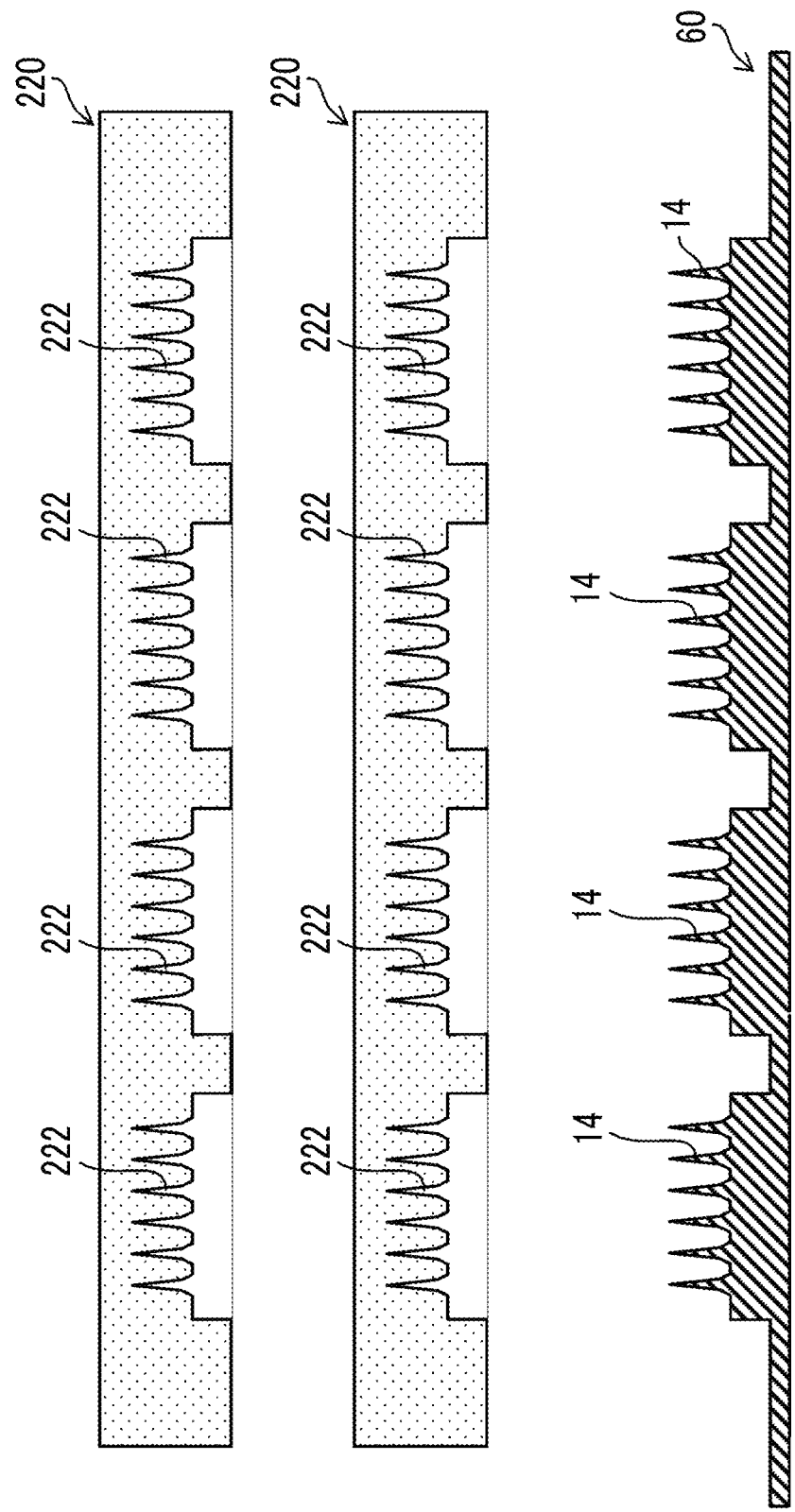
FIG. 33 is a view for describing a step of a manufacturing method of a second microneedle array.

As illustrated in FIG. 33, a large plate precursor 60 having a size corresponding to a plurality of patches of the microneedle array is prepared. The large plate precursor 60 has a plurality of the needle-like protrusions 14 for each size corresponding to one patch of the microneedle array. The resin mold 220 having a plurality of the needle-like recessed portions 222 is produced from the large plate precursor 60. The resin mold 220 can be produced, for example, by pouring a medical grade silicone material (for example, MDX4-4210 manufactured by Dow Corning) into the duplicate mold 210, performing a heating treatment thereon at 150° C. so as to be cured, and thereafter peeling off the resin mold 220 from the large plate precursor 60. The resin mold 220 can be produced from the large plate precursor 60 using the other method described in FIG. 28.

In the embodiment, the large plate precursor 60 can be produced within a short period of time by using the cutting tool 40. In the second manufacturing method of the microneedle array, steps of producing a resin precursor and a duplicate mold can be omitted.

EXPLANATION OF REFERENCES

10: plate precursor
12: base portion
12A: first surface
12B: second surface
14: needle-like protrusion
16: needle portion
18: frustum portion
20: protruding pattern
30: base material
30A: flat surface
40: cutting tool
42: blade
42A: frustum blade
42B: needle blade
42C: bottom surface blade
44: holder
50: uncut residue
60: large plate precursor
100: microneedle array
102: base portion
102A: first surface
102B: second surface
110: protruding pattern
112: needle-like protrusion
114: needle portion
116: frustum portion
200: resin precursor
202: recessed portion
204: needle-like recessed portion
210: duplicate mold
212: needle-like protrusion
220: resin mold 222: needle-like recessed portion
224: stepped portion
300: liquid material
P: pitch
r1: distance
r2: distance
NA: axis
TA: tool axis

What is claimed is:

1. A manufacturing method of a plate precursor having a needle-like protrusion, the method comprising:
   a preparation step of preparing a cutting tool comprising at least one blade conforming to an external shape of the needle-like protrusion, and a base material; and
   a cutting step of cutting the base material by rotating the cutting tool about a tool axis of the cutting tool and revolving the cutting tool around an axis of the needle-like protrusion to be formed on the base material to form the needle-like protrusion having a shape conforming to a shape of the cutting tool,
   wherein the cutting tool rotates about the tool axis at a position where a first distance is formed between the tool axis and the axis of the needle-like protrusion, the cutting tool revolves around the axis of the needle-like protrusion with the first distance as a first revolution radius, the at least one blade of the cutting tool cuts the base material to a predetermined depth,
   the cutting tool is moved in a direction away from the axis of the needle-like protrusion and the cutting tool rotates about the tool axis at a position where a second distance is formed between the tool axis and the axis of the needle-like protrusion, the cutting tool revolves around the axis of the needle-like protrusion with the second distance as a second revolution radius to cut the base material.

2. The manufacturing method of a plate precursor having a needle-like protrusion according to claim 1,
   wherein a plurality of the needle-like protrusions are formed by repeating the cutting step a plurality of times.

3. The manufacturing method of a plate precursor having a needle-like protrusion according to claim 1,
   wherein a distance between the tool axis and the axis is adjusted in the cutting step.

4. The manufacturing method of a plate precursor having a needle-like protrusion according to claim 1,
   wherein the cutting tool comprising at least one blade comprises a plurality of blades.

5. The manufacturing method of a plate precursor having a needle-like protrusion according to claim 1,
   wherein the cutting tool is moved to an inside of the base material stepwise in parallel to the tool axis, in the cutting step.

6. The manufacturing method of a plate precursor having a needle-like protrusion according to claim 5,
   wherein the stepwise movement of the cutting tool is a continuous movement.

7. The manufacturing method of a plate precursor having a needle-like protrusion according to claim 5,
   wherein the stepwise movement of the cutting tool is an intermittent movement.

8. The manufacturing method of a plate precursor having a needle-like protrusion according to claim 1,
   wherein the cutting tool is changed from a first posture to a second posture by inclining the tool axis to cut the base material by the cutting tool.

9. A manufacturing method of a microneedle array comprising:
   a step of preparing a plate precursor manufactured by the manufacturing method of a plate precursor having a needle-like protrusion according to claim 1;
   a step of producing a resin precursor having a needle-like recessed portion from the plate precursor;
   a step of producing a duplicate mold having a needle-like protrusion from the resin precursor by electroforming;
   a step of producing a resin mold having a needle-like recessed portion from the duplicate mold;
   a step of supplying a liquid material to the resin mold;
   a step of solidifying the liquid material of the resin mold by drying to form a microneedle array; and
   a step of separating the microneedle array from the resin mold,
   wherein the cutting tool rotates about the tool axis at a position where a first distance is formed between the tool axis and the axis of the needle-like protrusion, the cutting tool revolves around the axis of the needle-like protrusion with the first distance as a first revolution radius, the at least one blade of the cutting tool cuts the base material to a predetermined depth,
   the cutting tool is moved in a direction away from the axis of the needle-like protrusion and the cutting tool rotates about the tool axis at a position where a second distance is formed between the tool axis and the axis of the needle-like protrusion, the cutting tool revolves around the axis of the needle-like protrusion with the second distance as a second revolution radius to cut the base material.

10. A manufacturing method of a microneedle array comprising:
    a step of preparing a plate precursor manufactured by the manufacturing method of a plate precursor having a needle-like protrusion according to claim 1;
    a step of producing a resin mold having a needle-like recessed portion from the plate precursor;
    a step of supplying a liquid material to the resin mold;
    a step of solidifying the liquid material of the resin mold by drying to form a microneedle array; and
    a step of separating the microneedle array from the resin mold,
    wherein the cutting tool rotates about the tool axis at a position where a first distance is formed between the tool axis and the axis of the needle-like protrusion, the cutting tool revolves around the axis of the needle-like protrusion with the first distance as a first revolution radius, the at least one blade of the cutting tool cuts the base material to a predetermined depth,
    the cutting tool is moved in a direction away from the axis of the needle-like protrusion and the cutting tool rotates about the tool axis at a position where a second distance is formed between the tool axis and the axis of the needle-like protrusion, the cutting tool revolves around the axis of the needle-like protrusion with the second distance as a second revolution radius to cut the base material.

* * * * *